(12) United States Patent
Dadashian et al.

(10) Patent No.: US 12,115,376 B2
(45) Date of Patent: *Oct. 15, 2024

(54) IMPLANTABLE MEDICAL DEVICE INCLUDING WELDED SEPTUM ASSEMBLIES

(71) Applicant: Pacesetter, Inc., Sylmar, CA (US)

(72) Inventors: Asghar Dadashian, Porter Ranch, CA (US); Christopher R. Jenney, Valencia, CA (US)

(73) Assignee: Pacesetter, Inc., Sylmar (CA)

( * ) Notice: Subject to any disclaimer, the term of this patent is extended or adjusted under 35 U.S.C. 154(b) by 263 days.

This patent is subject to a terminal disclaimer.

(21) Appl. No.: 17/662,592

(22) Filed: May 9, 2022

(65) Prior Publication Data
US 2022/0257958 A1    Aug. 18, 2022

Related U.S. Application Data

(63) Continuation of application No. 16/836,582, filed on Mar. 31, 2020, now Pat. No. 11,351,384.

(51) Int. Cl.
*A61N 1/375*    (2006.01)
(52) U.S. Cl.
CPC ....... *A61N 1/37512* (2017.08); *A61N 1/3752* (2013.01); *A61N 1/3758* (2013.01)

(58) Field of Classification Search
CPC . A61N 1/37512; A61N 1/3752; A61N 1/3758
See application file for complete search history.

(56) References Cited

U.S. PATENT DOCUMENTS

| | | |
|---|---|---|
| 2003/0040780 A1 | 2/2003 | Haeg |
| 2004/0122481 A1 | 6/2004 | Tidemand |
| 2004/0215282 A1* | 10/2004 | Weijden ............... A61N 1/3752 607/37 |
| 2012/0123497 A1 | 5/2012 | Sherva |
| 2018/0166747 A1 | 6/2018 | Mouchawar |

* cited by examiner

*Primary Examiner* — Eugene T Wu
(74) *Attorney, Agent, or Firm* — Dean D. Small; The Small Patent Law Group

(57) ABSTRACT

An implantable medical device includes a header body and a septum assembly. The header body includes a first welding surface and a septum bore extending inwardly from an outer surface to an inner cavity. The septum assembly is at least partially disposed within the septum bore of the header assembly and includes a septum configured to allow insertion of a tool through the septum into the inner cavity and to otherwise provide a seal. The septum assembly further includes a retainer within which at least a portion of the septum is retained. The retainer includes a welding feature coupled to the retainer body, the welding feature providing a second welding surface. The retainer is coupled to the header body by welding the first welding surface to the second welding surface.

20 Claims, 18 Drawing Sheets

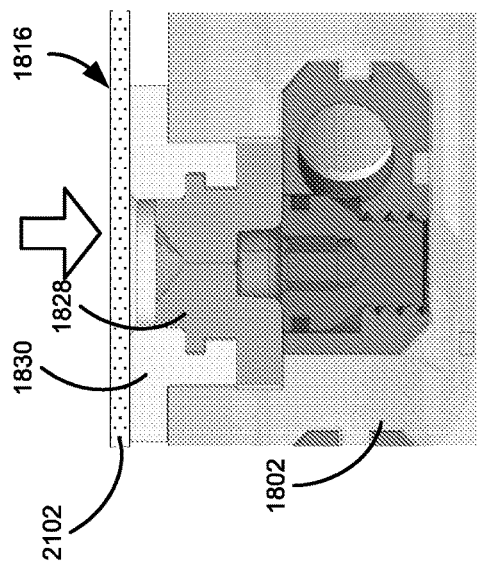
FIG. 21A
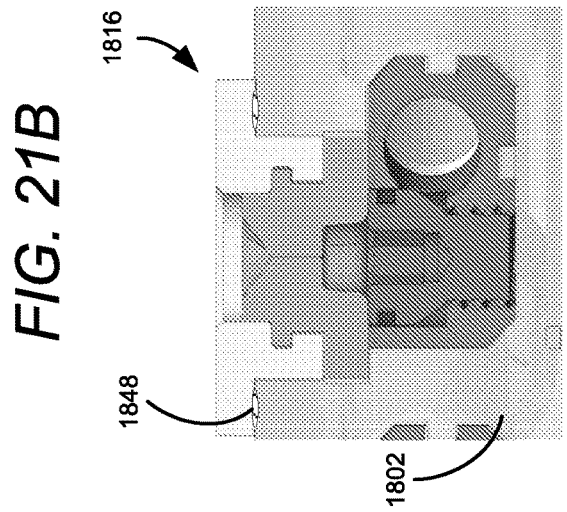
FIG. 21B
FIG. 21C
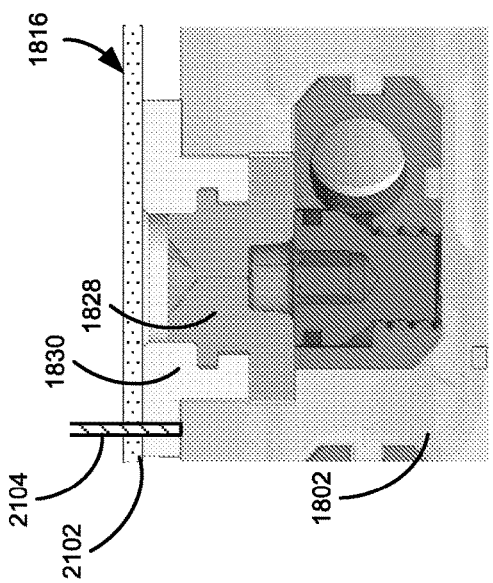
FIG. 21D

IMPLANTABLE MEDICAL DEVICE INCLUDING WELDED SEPTUM ASSEMBLIES

CROSS-REFERENCE TO RELATED APPLICATION

This application is a continuation of U.S. patent application Ser. No. 16/836,582, filed Mar. 31, 2020, which is incorporated by reference herein in its entirety.

BACKGROUND

Embodiments of the present disclosure generally relate to medical apparatus. More specifically, the embodiments relate to an implantable electronic device including a header and septum assemblies to enable access to an internal volume of the header, the septum assemblies being welded to the header.

Implantable electronic devices (IEDs) include implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems. These IPGs commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

A header of an IPG encloses the connector assembly, which has many internal electrically conductive components such as, for example, wires, ribbon, antennas, blocks, rings, etc. The connector assembly further includes one or more connector blocks into which terminal ends of leads may be inserted. In certain IPGs, the connector blocks or adjacent structures may include setscrews that may be tightened after insertion of a terminal lead end to fix the terminal lead end.

The setscrews may be disposed within an internal cavity of the header. A seal may be provided to prevent communication of electrical signals as well as bodily or other fluids into the internal cavity of the header; however, such a seal must permit access to the set screw in the event the leads of the IPG are to be disconnected from the header.

It is with the foregoing in mind that the following concepts were conceived and developed.

SUMMARY

In one aspect of the present disclosure, an implantable medical device including a header body and a septum assembly is provided. The header body includes a first welding surface, an outer surface, an inner cavity, and a septum bore extending inwardly from the outer surface to the inner cavity. The septum assembly is at least partially disposed within the septum bore of the header assembly and includes a septum configured to allow insertion of a tool through the septum into the inner cavity and to provide a seal when the tool is not inserted through the septum. The septum assembly further includes a retainer having a retainer body within which at least a portion of the septum is retained. The retainer further includes a welding feature coupled to the retainer body, the welding feature providing a second welding surface. The retainer is coupled to the header body by ultrasonically welding the first welding surface to the second welding surface.

In one implementation, the welding feature is a flange extending laterally from the retainer body.

The first welding surface may, in certain implementations, be a portion of the outer surface of the header body. In another implementation, the first welding surface may be disposed within the septum bore. In such implementations, the septum bore may include a counter bore and the first welding surface may be at least a portion of a bottom surface of the counter bore.

In some implementations, prior to being welded, at least one of the first welding surface and the second welding surface includes an energy director extending therefrom such that when welded, the energy director at least partially forms a joint between the retainer and the header body. In such implementations, the energy director may be a protrusion extending from the at least one of the first welding surface and the second welding surface. Alternatively, the energy director may be a textured portion of the at least one of the first welding surface and the second welding surface.

In other implementations, the first welding surface and the second welding surface may be formed from respective transparent thermoplastic materials, such as, thermoplastic polyether polyurethane.

In still other implementations, the header body may further include an insert that includes the first welding surface and at least partially defines the septum bore.

In yet other implementations, the septum may be disposed entirely below the outer surface of the header body. A set screw may also be disposed within the inner cavity of the header body.

In another implementation, the implantable medical device may further include a sealing element disposed between the retainer and the header body, the sealing element providing a fluid seal between the retainer and the header body.

In another aspect of the present disclosure, a method of manufacturing an implantable electronic device (IED) is provided. The method includes disposing a septum assembly in a bore of a header body of the IED, the septum assembly including a septum and a retainer, the septum assembly disposed in the bore such that the septum is at least partially disposed within the bore and the retainer abuts a surface of the header body. The method further includes ultrasonically welding the retainer to the header body.

In one implementation, the retainer includes a body and a flange extending from the body such that when the septum assembly is disposed in the bore, the flange abuts an outer surface of the header body when the septum assembly is disposed within the bore and ultrasonically welding the retainer to the header body includes ultrasonically welding the flange to the outer surface.

In another implementation, the bore includes a counter bore having a bottom surface and ultrasonically welding the retainer to the header body includes ultrasonically welding the retainer to the bottom surface of the counter bore.

In yet another implementation, the method includes disposing a sealing element between the retainer and the header body prior to ultrasonically welding the retainer to the header body. In such implementations, the sealing element may be an elastomeric ring or may be a portion of the septum.

In still another implementation, the retainer includes an energy director, and ultrasonically welding the retainer to the header body results in the energy director melting to join the retainer to the header body.

In another aspect of the present disclosure, another implantable medical device including a header body and a septum assembly is provided. The header body includes a first welding surface, an outer surface, an inner cavity, and a septum bore extending inwardly from the outer surface to the inner cavity. The septum assembly is at least partially disposed within the septum bore of the header assembly and includes a septum configured to allow insertion of a tool through the septum into the inner cavity and to provide a seal when the tool is not inserted through the septum. The septum assembly further includes a retainer having a retainer body within which at least a portion of the septum is retained. The retainer further includes a welding feature coupled to the retainer body, the welding feature providing a second welding surface. The retainer is coupled to the header body by laser welding the first welding surface to the second welding surface.

In one implementation, the welding feature is a flange extending laterally from the retainer body.

The first welding surface may, in certain implementations, be a portion of the outer surface of the header body. In another implementation, the first welding surface may be disposed within the septum bore. In such implementations, the septum bore may include a counter bore and the first welding surface may be at least a portion of a bottom surface of the counter bore.

In other implementations, the first welding surface and the second welding surface may be formed from respective transparent thermoplastic materials, such as, thermoplastic polyether polyurethane.

In still other implementations, the header body may further include an insert that includes the first welding surface and at least partially defines the septum bore.

In yet other implementations, the septum may be disposed entirely below the outer surface of the header body. A set screw may also be disposed within the inner cavity of the header body.

In another implementation, the implantable medical device may further include a sealing element disposed between the retainer and the header body, the sealing element providing a fluid seal between the retainer and the header body.

In another aspect of the present disclosure, a method of manufacturing an implantable electronic device (IED) is provided. The method includes disposing a septum assembly in a bore of a header body of the IED, the septum assembly including a septum and a retainer, the septum assembly disposed in the bore such that the septum is at least partially disposed within the bore and the retainer abuts a surface of the header body. The method further includes laser welding the retainer to the header body at an interface between the retainer and the header body by passing a laser through the retainer to the interface.

In one implementation, the retainer includes a body and a flange extending from the body such that when the septum assembly is disposed in the bore, and the laser is passed through the flange.

In another implementation, the bore includes a counter bore having a bottom surface and the interface is between the retainer and the bottom surface of the counter bore.

In yet another implementation, the method further includes, prior to laser welding the retainer to the header body, disposing a sealing element between the retainer and the header body. The sealing element may be, for example, one of an elastomeric ring and a portion of the septum.

In still another implementation, the method further includes, prior to laser welding the retainer to the header body, applying pressure to the septum assembly such that the septum assembly is forced into the bore. In one such implementation, the pressure is applied by a plate and the laser is further passed through the plate.

In another implementation laser welding the retainer to the header body includes welding the retainer to the header body using a fiber laser. In certain implementations, the fiber laser has a wavelength of approximately two-microns.

BRIEF DESCRIPTION OF THE DRAWINGS

FIG. 21A-21D are detailed cross-sectional views of the septum assembly of FIG. 18 at different stages of manufacturing the septum assembly;

DETAILED DESCRIPTION

Figure 1:
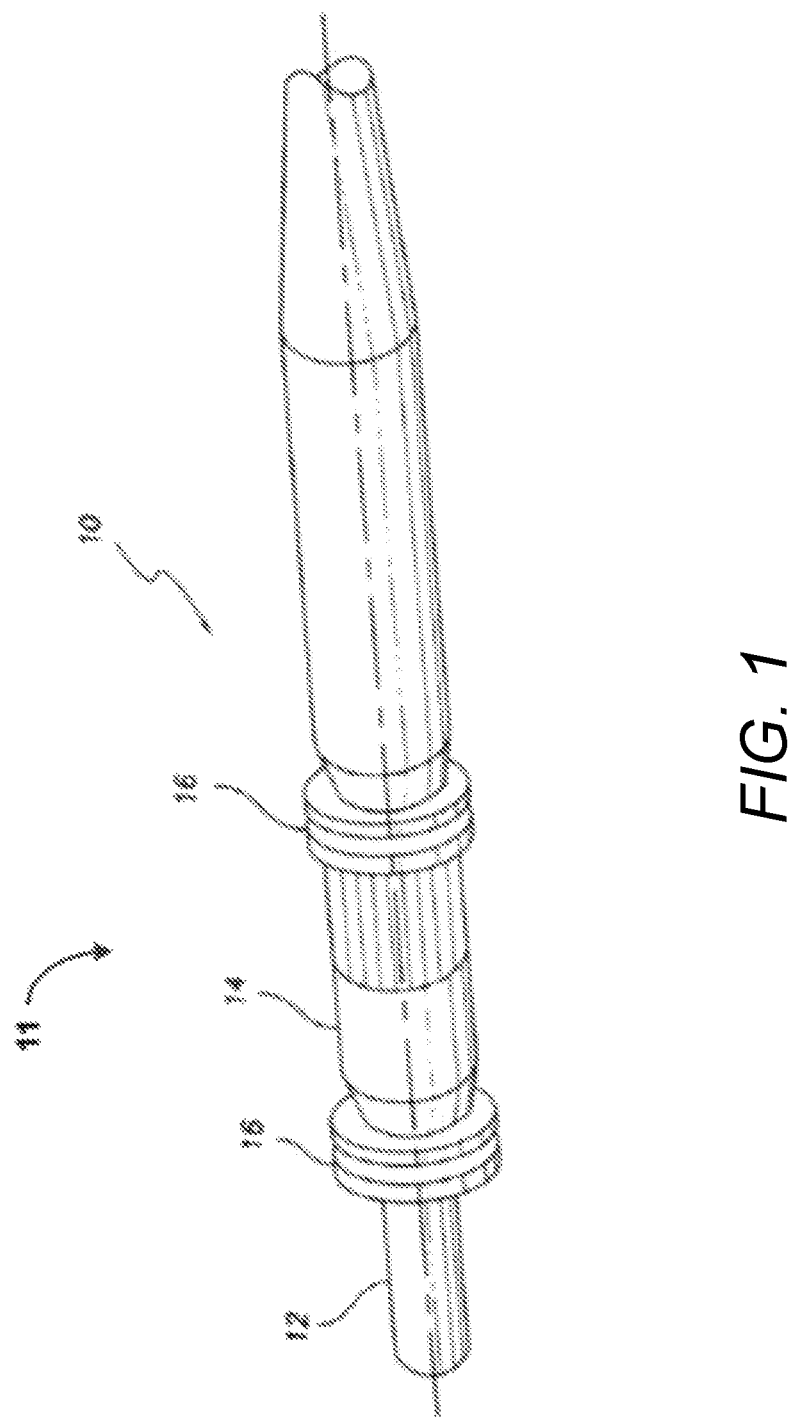
FIG. 1 is an isometric view of a proximal end portion (i.e., lead connector end) of a transvenous bipolar pacing lead.

Implementations of the present disclosure involve an implantable electronic device (IED) such as an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

Setscrews may be used in the headers to secure leads in place within corresponding lead bores or connector blocks. To facilitate access to the setscrews, implantable medical devices in accordance with the present disclosure include septum assemblies disposed within a header body of the header. Each septum assembly includes a retainer that is coupled to the header body when the header is assembled and a septum that permits access to the setscrews using a torque driver or other tool. When the tool is not present, the septum provides a seal, thereby preventing ingress of electrical signals and bodily or other fluid into the internal cavity of the header body. The retainer couples to the header body to keep the septum at least partially disposed within the header body.

In implementations of the present disclosure, the retainer of the septum assembly is configured to be welded to the header body, such as by ultrasonic or laser welding. To do so, each of the header body and the retainer is at least partially formed from an weldable material, such as thermoplastic polyether polyurethane. Each of the retainer and header body may further include specific surfaces adapted to facilitate welding of the two components. For example, in one implementation, the retainer includes a flange that abuts the outer surface of the header body when the septum assembly is inserted into a septum assembly bore of the header body. The retainer is then coupled to the header body by welding the abutting surfaces of the flange and header body.

In other implementations, other surfaces of the retainer and header body may be joined by the welding process. For example, in at least one implementation the septum bore of the header body includes a counter bore within which the retainer is seated such that a surface of the retainer abuts the bottom of the counter bore. The retainer is then welded to the bottom of the counter bore.

As further described below, in implementations involving ultrasonic welding, the header body and/or the retainer may include one or more energy directors to facilitate welding of the two components. In general, an energy director is a protrusion or series of protrusions that form the initial contact between the two components. During the ultrasonic welding process, the energy director focuses the applied ultrasonic energy, melting the energy director to form a joint between the two components. Accordingly, implementations of the current disclosure include various arrangements of energy directors to facilitate joining of the retainer and header body at various locations.

The foregoing and other features of the present disclosure regarding implementation of the septum assemblies are provided below in further detail. However, for purposes of context, a general overview of lead connectors, IPG devices and IPG device headers is provided. It should be noted that the following overview is provided primarily for context and should not be viewed as limiting the present disclosure to applications involving any of the specific example IPG devices discussed.

A. Overview of Lead Connector End and IPG

FIG. 1 shows a proximal end portion 10 of a transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consist of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane elastomers. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, including a pair of coaxial spaced-apart electrical terminals including a tip terminal 12 and a ring terminal 14. The tip terminal 12 is electrically connected via of the inner conductor coil to the tip electrode at the distal end of the lead, while the ring terminal 14 is electrically connected to the anodal ring electrode via of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
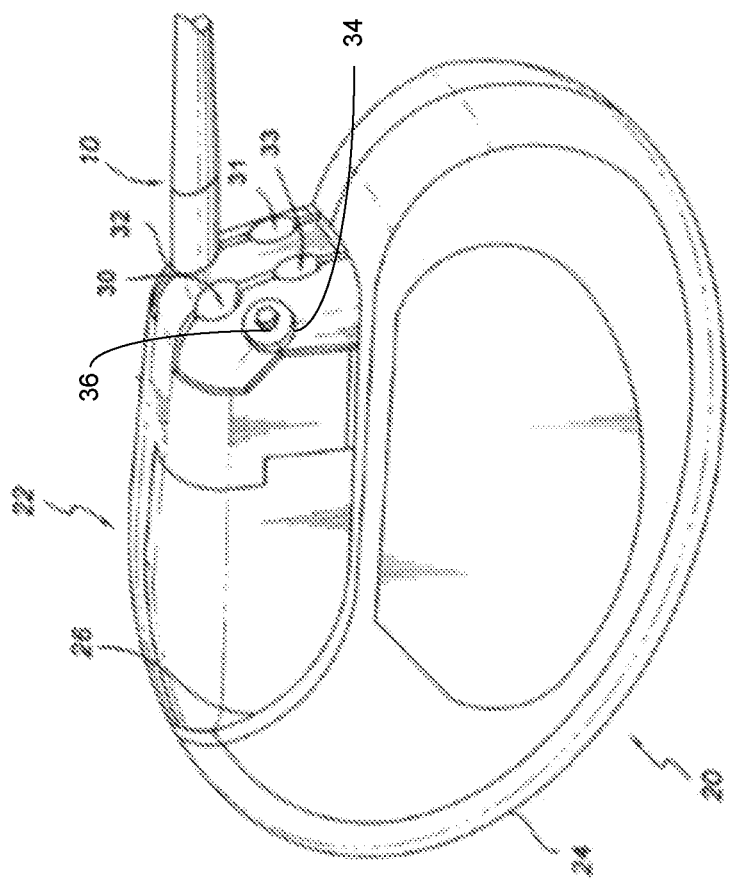
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3, 4A and 4B discussed below. The IPG 20 includes a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes a single pair of receptacles (i.e., receptacles 30 and 33) for receiving the proximal ends of leads such as, for example, conventional bipolar leads and/or conventional cardioverting and/or defibrillating leads. One or more setscrews 36 may be threadedly received in respective setscrew bores 34 to secure the proximal end portion 10 of the lead in the header connector assembly 22, as discussed in greater detail below.

Figure 3:
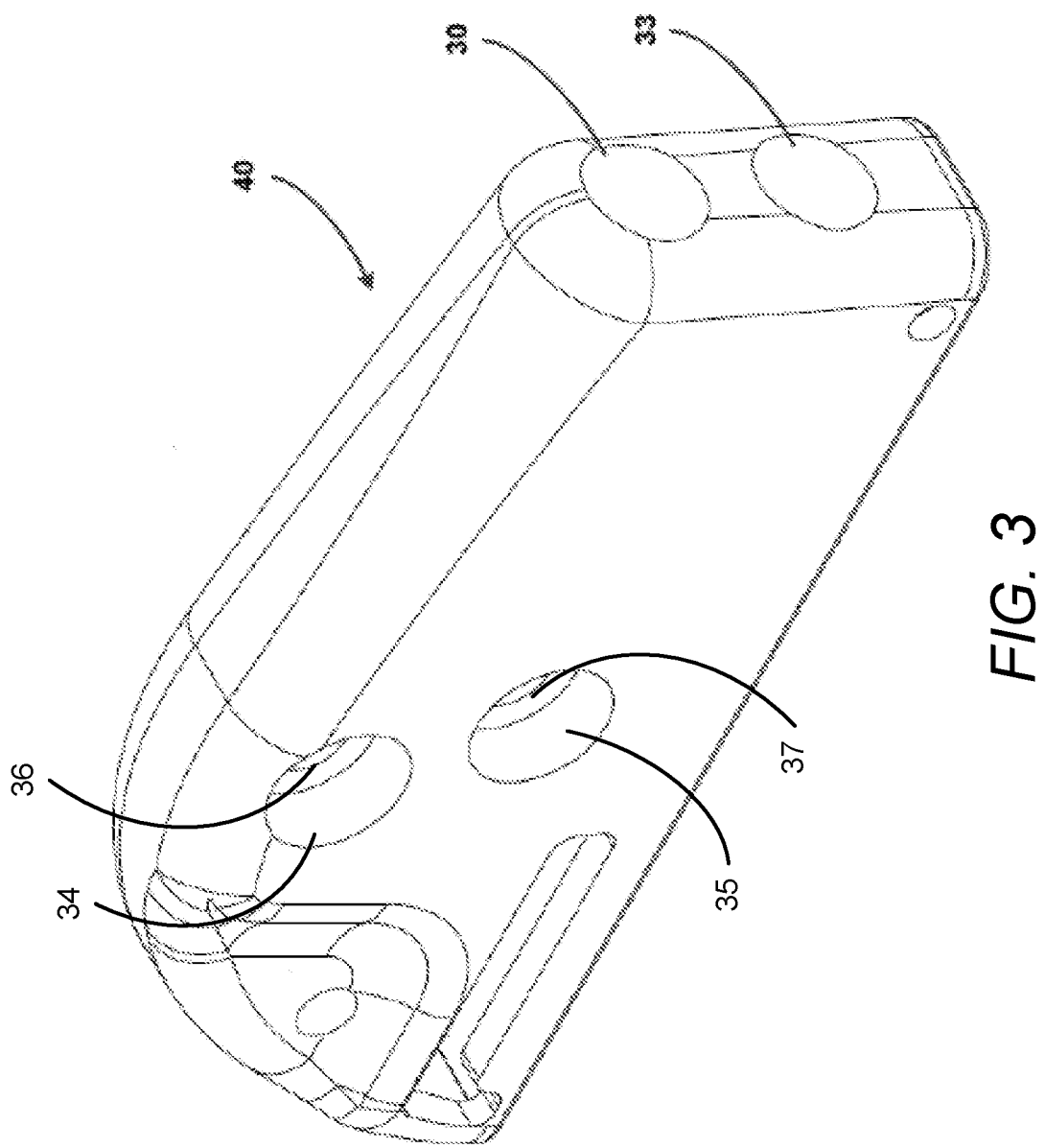
FIG. 3 is an isometric view of a representative header.
Figure 4A:
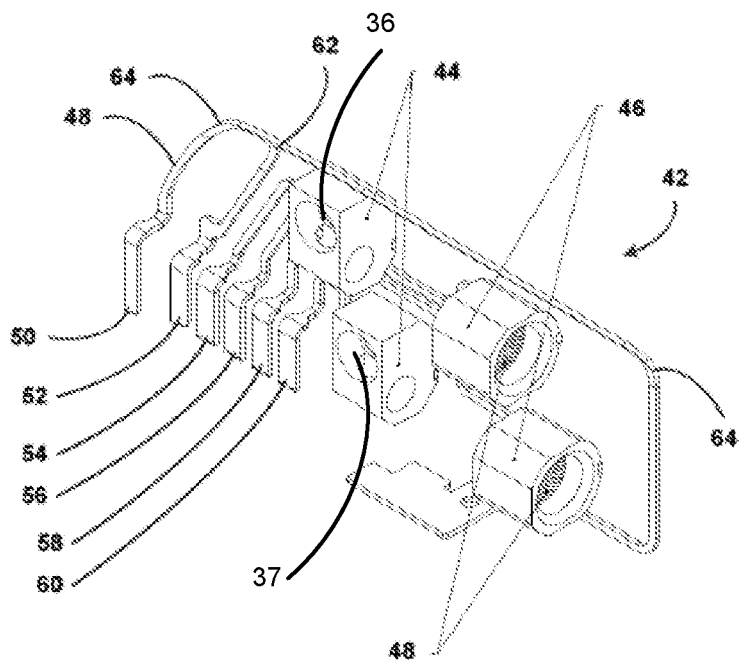
FIGS. 4A and 4B are opposite isometric views of a representative connector assembly used with the header of FIG. 3 to form a header connector assembly.
Figure 4B:
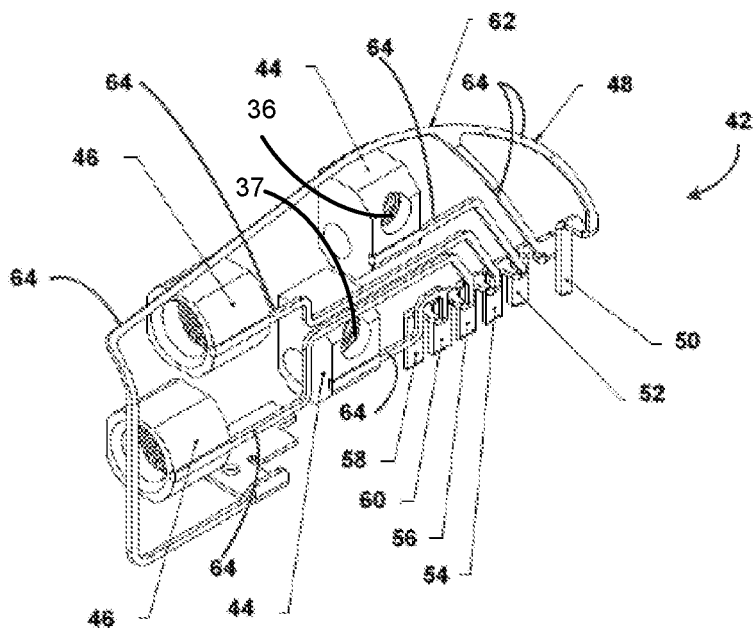

FIG. 3 is an isometric view of a representative header 40, and FIGS. 4A and 4B are opposite isometric views of a representative connector assembly 42. Unlike the header connector assembly 22 of FIG. 2, the header 40 of FIG. 3 only has a single pair of receptacles 30 and 33. However, in other embodiments, the header 40 of FIG. 3 may have any suitable number of receptacles including, but not limited to, two or more pairs similar to the embodiment of FIG. 2.

Each receptacle 30, 33 is adapted to receive a proximal end of a lead, such as the proximal end portion 10 illustrated in FIG. 1. As shown in FIG. 3, the header 40 further defines a pair of setscrew bores 34, 35 corresponding to the receptacles 30, 33, respectively. Corresponding setscrews 36, 37 are disposed within the setscrew holes 34, 35 such that when proximal lead ends are fully inserted into the receptacles 30, 33, the setscrews 36, 37 may be tightened to retain the proximal lead ends within the header 40. For clarity and context, FIG. 3 omits septums from the header 40, however, when the header 40 is fully assembled, septums are disposed within the setscrew bores 34, 35. An example of an assembled header with septums included is described below in the context of FIG. 5.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIGS. 4A and 4B, the connector assembly 42 also includes a host of electrically conductive components including an antenna 48, a RF anchor tab 50, a RF pin tab 52, an A-tip tab 54, an A-ring tab 56, a RV-ring tab 58, a RV-tip tab 60, and a ribbon carrier 62 and other conductors 64 that extend between the various tabs and their respective electrical contacts of the connector assembly or other components thereof. In other words, as can be understood from FIGS. 4A and 4B, electrical conductor elements (e.g., wires, traces, or other electrical conductors) 64 extend between the electrical blocks 44, 46 and the respective tabs 50, 52, 54, 56, 58 and 60. Also, such conductor elements 64 may form the antenna 48 and the ribbon carrier 62.

The various tabs are welded to corresponding terminals extending from circuitry of the IPG 20 contained in the housing 24 of the IPG 20 depicted in FIG. 2 when the header connector assembly 22 is joined with the housing 24 to form the IPG 20. The connector assembly 42 is manufactured of materials and via methods known in the industry. The connector assembly 42 is cast in place, injected molded or otherwise installed into the header 40 to form the header connector assembly 22 of FIG. 2, which can be considered a first module that is then attached via a backfill or other process to a second module in the form of the housing 24. In other words, the header connector assembly 22 (i.e., first module) is attached via a backfill or other process to the housing 24 (i.e., the second module) to form the IPG 20.

The foregoing discussion is intended merely to provide context for the current disclosure. Accordingly, any specific configurations or devices discussed above or illustrated in the corresponding figures should be regarded merely as illustrating non-limiting implementations of the present disclosure. More generally, the current disclosure is applicable to any implantable medical device for which access to at least a portion of the device is facilitated by a septum or similar sealing mechanism. Accordingly, the current disclosure should not be regarded as being limited to ICD/IPG devices or any of the specific example devices described herein or their respective features. For example, devices in accordance with the present disclosure may include any suitable number of septums for accessing internal portions of the device which may be arranged in any suitable configuration. Moreover, while the current disclosure refers generally to septums used to access set screws, the septums described herein may be used to access any internal component or volume of an implantable device header.

B. Header Assemblies Including Ultrasonically Welded Septum Assemblies

Figure 5:
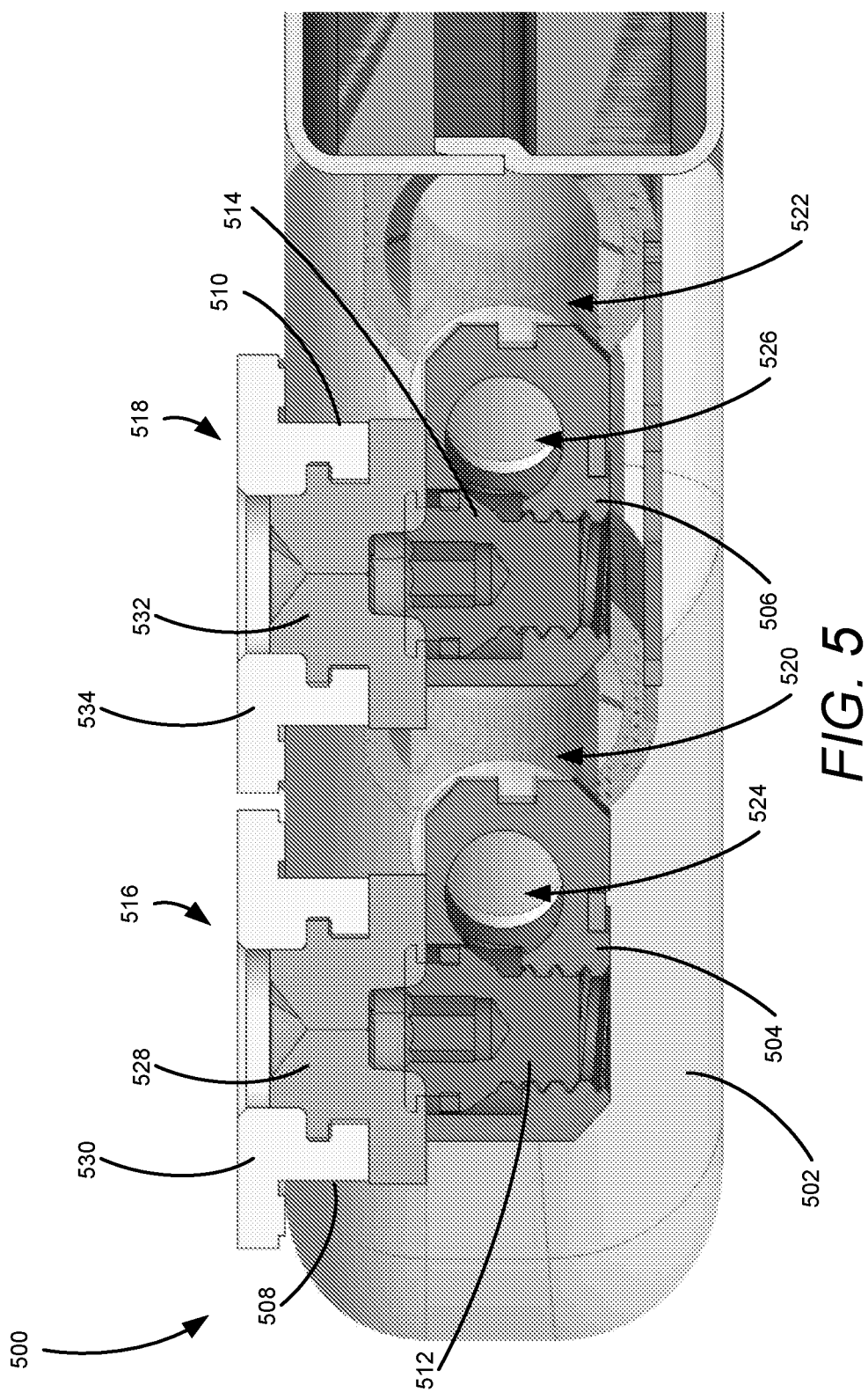
FIG. 5 is a cross-sectional view of a header including septum assemblies.

FIG. 5 is a partial cross-sectional view of a header assembly 500 in accordance with the present disclosure. As illustrated, the header assembly 500 includes a header body 502 within which a pair of tip blocks 504, 506 is disposed. As previously discussed, the tip blocks 504, 506 are configured to receive a lead tip, such as the tip terminal 12 of the connector end 11 illustrated in FIG. 1.

To facilitate retention of the lead tips when received within the tip blocks 504, 506, the header body 502 defines septum bores 508, 510 within which set screws 512, 514 and septum assemblies 516, 518 may be disposed. As illustrated in FIG. 5, the septum bores 508, 510 may extend perpendicular to connector bores 520, 522 such that the set screws 514, 516 are disposed adjacent to connector tip receiving bores 524, 526 of the tip blocks 504, 506.

When a tip terminal is received within one of the tip blocks 504, 506 the respective set screw 512, 514 may be screwed further into the tip block 504, 506 such that the set screw 512, 514 contacts and interferes with the tip terminal, thereby retaining the tip terminal within the tip block 504, 506. If the connector is to be removed, the set screw 512, 514 may be counter-rotated or unscrewed such that the tip terminal may be pulled out of the tip block 504, 506.

The septum assemblies 516, 518 are configured to enable insertion of a tool for rotating and counter-rotating the set screws 512, 514 and to provide a seal when the tool is not present. As illustrated in FIG. 5, a first septum assembly 516 includes each of a first flexible septum 528 and a first retainer 530 while a second septum assembly 518 includes each of a second flexible septum 532 and a second retainer 534.

The following discussion focuses on the first septum assembly 516 and its various components and, as a result, refers to the first septum assembly 516 simply as the septum assembly 516, the first septum 528 as the septum 528, and the first retainer 530 as the retainer 530. It should be understood that the following discussion regarding the first septum assembly 516 generally applies to the second septum assembly 518 unless otherwise noted. While the header assembly 500 is illustrated in FIG. 5 and subsequent figures as including only two septum assemblies 516, 518, it should be appreciated that in other implementations of the present disclosure, the header assembly 500 may include more or fewer set screws and, as a result, a corresponding number of septum assemblies may be included. Moreover, while the current disclosure focuses primarily on the use of the disclosed septum assemblies for purposes of enabling ingress into the header assembly 500 of a tool for manipulating the set screws 512, 514, it should be further appreciated that the current disclosure may be used in other applications or devices, including for other medical devices, in which access occasionally be required into the device but that otherwise requires the device be sealed.

Figure 6:
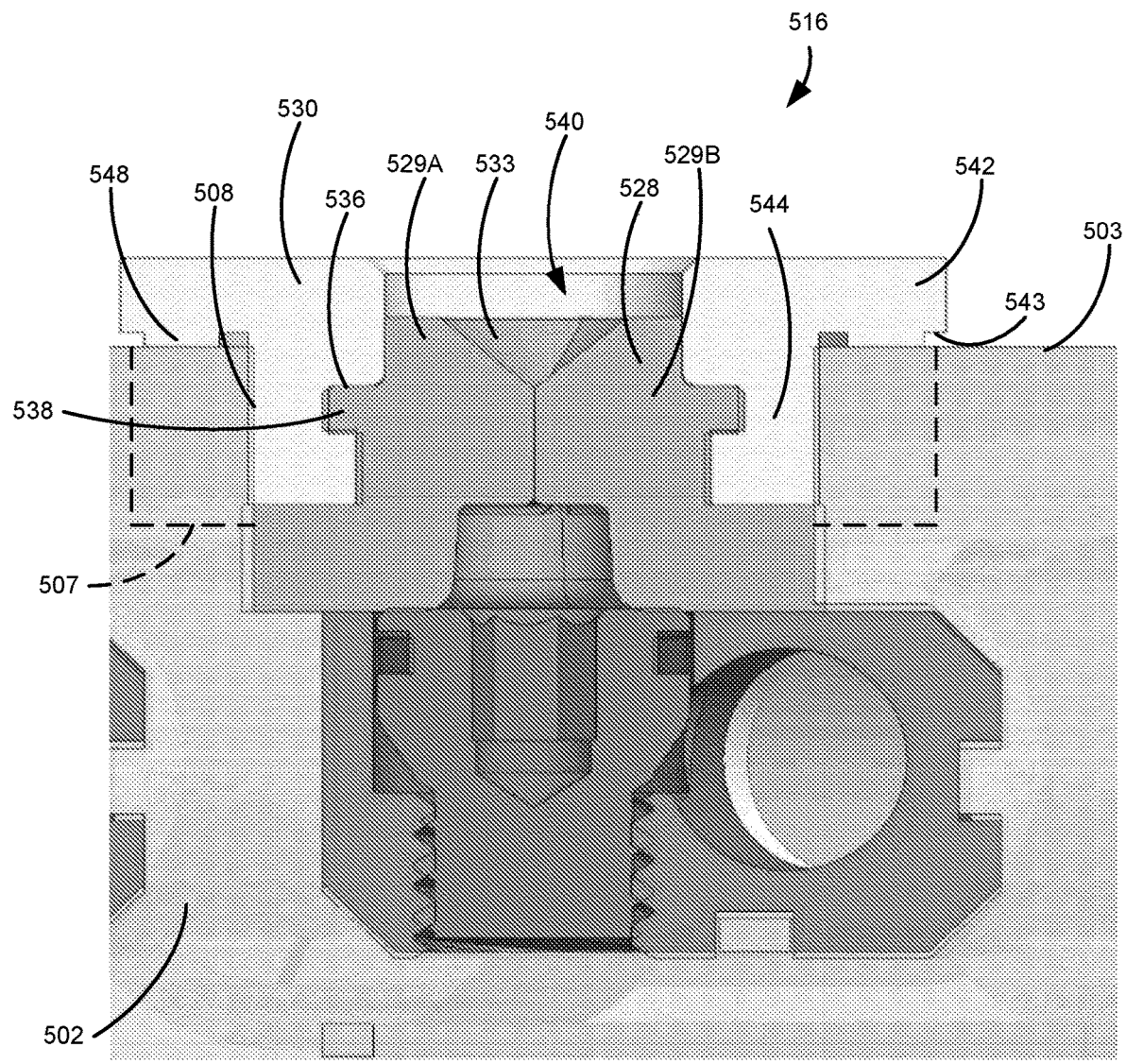
FIG. 6 is a detailed cross-sectional view of the septum assembly of FIG. 5.
Figure 7:
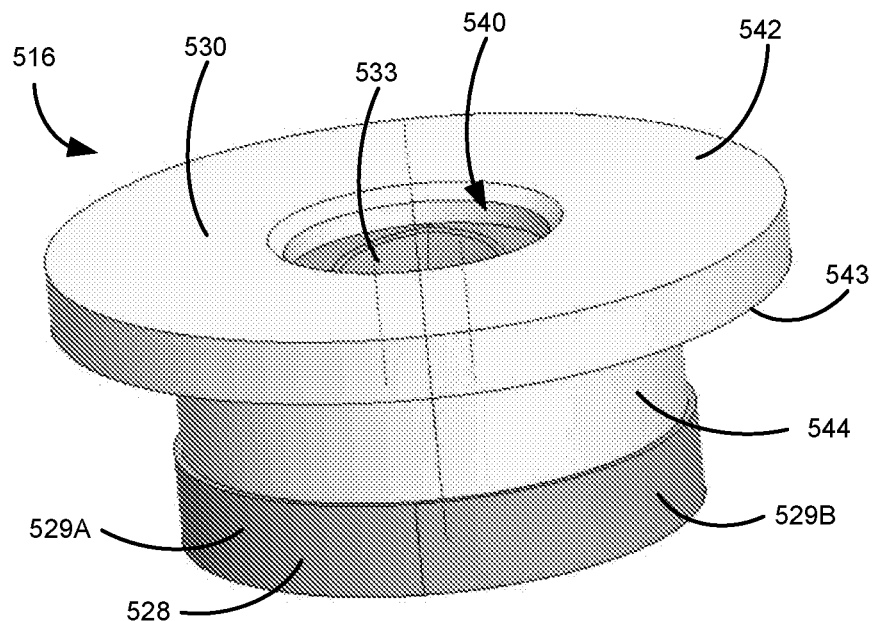
FIG. 7 is an isometric view of the septum assembly of FIG. 6.
Figure 8:
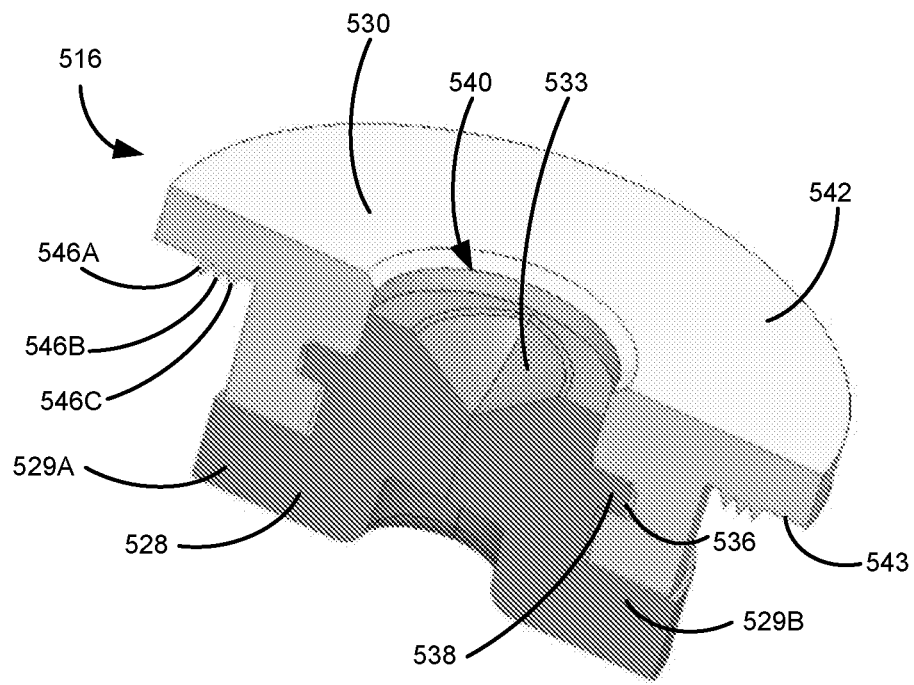
FIG. 8 is an isometric cross-sectional view of the septum assembly of FIG. 6.
Figure 9:
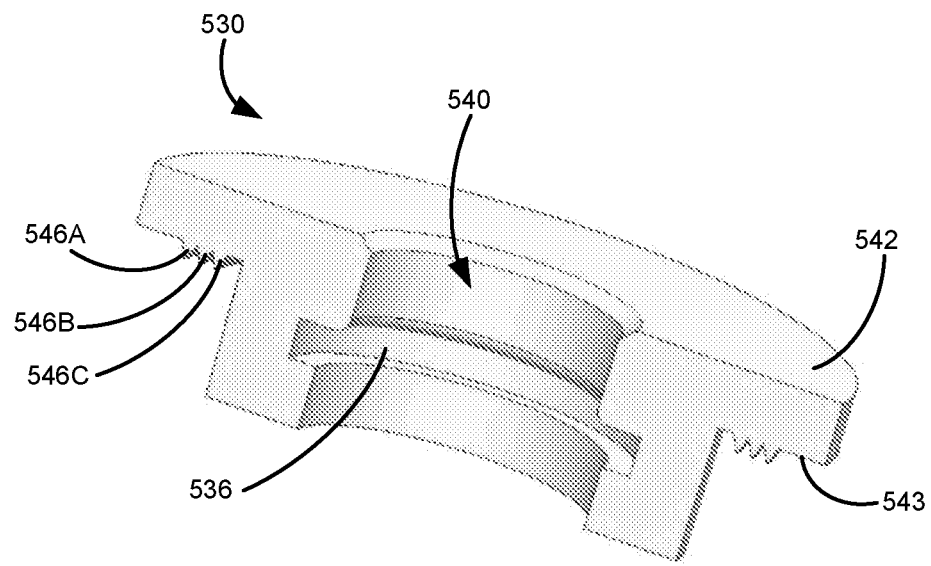
FIG. 9 is an isometric cross-sectional view of a retainer of the septum assembly of FIG. 6.

Reference is now made to FIGS. 6-11, which provide additional details regarding the septum assembly 516. FIG. 6 is a detailed view of the septum assembly 516 as disposed within the header body 502 of the header assembly shown in FIG. 5; FIGS. 7 and 8 are isometric and isometric cross-sectional views of the septum assembly 516, respectively; and FIG. 9 is a cross-sectional view of the retainer 530. For purposes of the following discussion, like reference numbers are used to refer to the same features or elements in each figure. Accordingly, to the extent a reference number is indicated in a particular figure but not discussed in detail with respect to that figure, it should be understood to generally correspond to similarly numbered elements in other figures.

As previously noted, the septum assembly 516 includes each of a septum 528 and a retainer 530. The septum 528 is generally formed of a flexible material, such as, but not limited to, silicone rubber. The septum 528 may be split into two or more pieces or otherwise include a puncture or slit extending through the septum 528 to enable insertion of tools through the septum 528. For example, in the implementation of FIG. 6, the septum 528 includes each of a first septum half 529A and a second septum half 529B. Also, as shown in FIG. 6, the septum 528 may include a guide surface 533 for directing tools toward the center of the septum 528.

The retainer 530 of the septum assembly 516 retains the septum 528 and couples the septum assembly to the header body 502. With respect to retaining the septum 528, the retainer 530 may include one or more channels, grooves, or similar features that mate with corresponding features of the septum 528 such that the septum 528 may be inserted into and held within the retainer 530. For example, as shown in FIG. 6, the retainer 530 includes an inner circumferential groove 536 within which an outer circumferential protrusion 538 of the assembled septum 528 is inserted. In implementations in which the septum 528 includes multiple pieces, the retainer 530 also servers to maintain the multiple pieces in proper relation to each other. The retainer 530 further defines a bore 540 extending therethrough such that a tool may access the septum 528.

Coupling of the retainer 530 to the header body 502 may be achieved in various ways; however, in general, the retainer 530 includes a feature or surface that abuts a corresponding surface or feature of the header body 502 when the septum assembly 516 is inserted into the septum assembly bore 508. Once inserted, the retainer 520 is joined to the header body 502. In the following examples, such joining is accomplished using ultrasonic welding; however, as discussed later in this disclosure, other techniques, such as laser welding, may also be used.

In the specific example illustrated in FIG. 6 and FIG. 7, the retainer 530 includes a flange 542 that extends radially outward from a body 544 of the retainer 530. When the septum assembly 516 is disposed within the septum assembly bore 508, the flange 542 extends beyond the septum assembly bore 508 and abuts an outer surface 503 of the header body 502. Once positioned within the septum assembly bore 508, a welding surface 543 of the flange 542 may be joined to the outer surface 503 of the header body 502, such as by ultrasonic welding. As a result of such joining, the septum assembly 516 is fixed to the header body 502 and the septum 528 is retained in its proper location.

Although illustrated as being a unitary component, the header body 502 may alternatively include a primary structure within which multiple inserts are disposed. The general location and extent of an example of such an insert is indicated in FIG. 6 by dashed line 507. As illustrated, the insert may generally replace a portion of the header body 502 of FIG. 6 that defines at least a portion of the septum assembly bore 508. Moreover, the insert may also provide the surface to which the retainer 530 is welded. Among other things, the use of inserts provides flexibility regarding material choice. More specifically, the inclusion of inserts formed from weldable materials, permits the remainder of the header body 502 to be formed from materials that, while advantageous for manufacturing or other reasons, may not be readily weldable to the retainer 530. In certain implementations, the insert and the header body 502 may be formed of a specific material amenable to ultrasonic welding or other bonding with the retainer 530.

In certain implementations, joining of the septum assembly 516 to the header body 502 may be facilitated by including one or more energy directors or similar welding feature coupled to the retainer 530 or the header body 502. In general, the welding feature is coupled to the retainer 530 or the header body 502 by being integrally formed with the retainer 530 or the header body 502; however, in other implementations, the welding feature may be a separate component that is attached to the retainer 530 or the header body 502. In general, an energy director is a protrusion or similar feature that limits initial contact between surfaces being welded and focuses energy applied to the surfaces at one or more apexes or similar terminal locations of the energy director.

For example, ultrasonic and similar welding processes are generally performed using a press-like machine. The components to be joined are loaded into the machine such that the surfaces to be joined are abutting or otherwise aligned. In most cases, one component is disposed between a rigid body (e.g., a nest, jig, or anvil) and the second component. A sonotrode is then translated to abut the second component and apply pressure to the components while ultrasonic energy is provided to the sonotrode. The vibrations of the sonotrode are transmitted through the second component causing the abutting surfaces of the components to melt and the material of the two components to flow together, thereby bonding the components. By implementing energy directors, the energy from the sonotrode can be directed to specific locations and can also lead to more rapid bonding between the components due to the lower surface area of the energy director as compared to the full surfaces of the components.

As illustrated in FIGS. 8 and 9, the retainer 530 includes an energy director 544 extending from the welding surface 543 of the flange 540. The energy director 544 is illustrated as a set of concentric triangular rings 546A-546C. Accordingly, when assembling the septum assembly 516 to the header body 502, contact is first made between the outer surface 503 of the header body 502 and the rings 546A-546C of the energy director 544. As ultrasonic energy is provided to the retainer 530, the ultrasonic energy is directed to the rings 546A-546C, causing them to melt and join the retainer 530 to the header body 502. As shown in FIG. 6, the result may be a weld bead or joint 548 formed between the retainer 530 and the header body 502.

Figure 10:
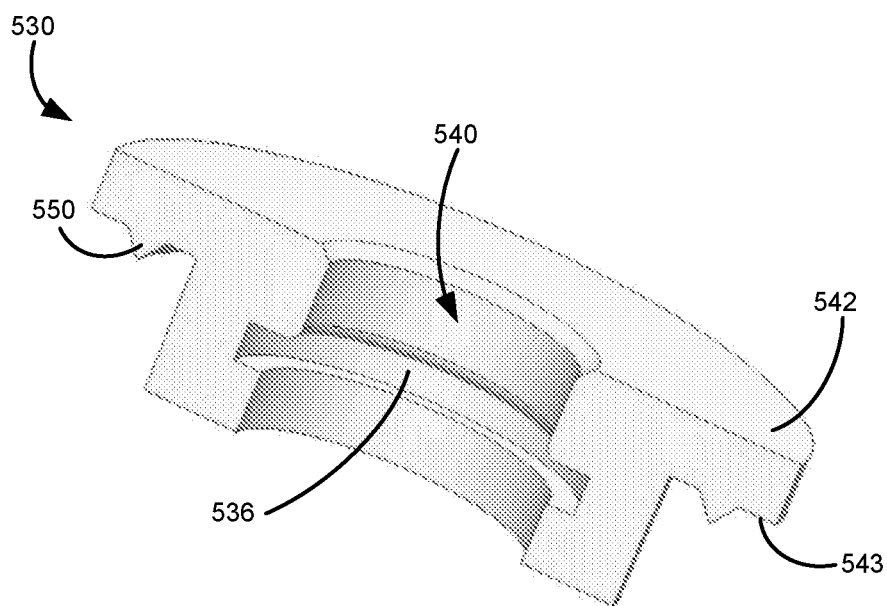
FIG. 10 is an isometric cross-sectional view of an alternative retainer for use in the septum assembly of FIG. 6 including a single triangular energy director.

The three-ring energy director of FIG. 9 is intended merely as an example of energy directors that may be used in implementations of the present disclosure. FIG. 10, for example, is a cross-sectional view of an alternative implementation of the retainer 530 in which the concentric rings 546A-546C has been replaced by a single triangular ring 550 extending circumferentially about the welding surface 543 of the flange 542.

The energy directors illustrated in FIGS. 9 and 10, which include triangular protrusions extending from the flange 540 about the retainer 530, are simply two examples of possible energy directing features that may be used in implementations of the present disclosure. In other implementations, one or both of the retainer 530 and the outer surface 503 of the header body 502 may include other energy director configurations.

Figure 11:
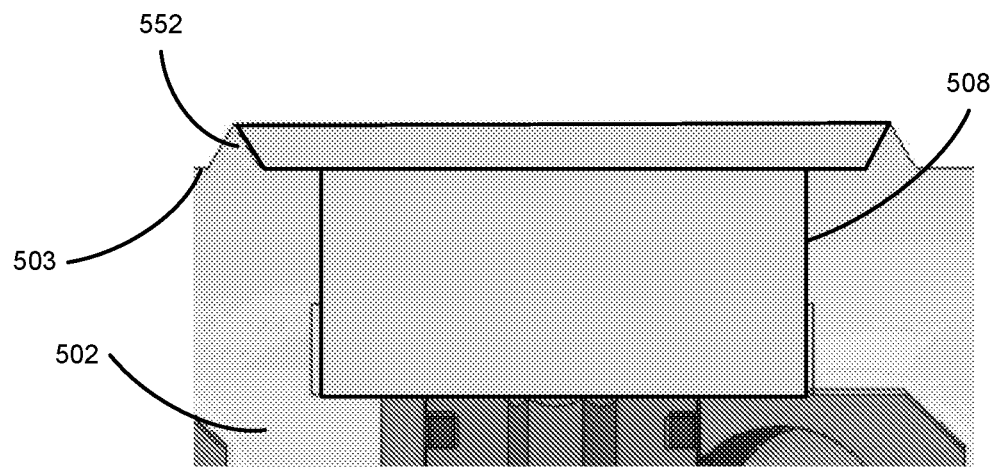
FIG. 11 is a detailed cross-sectional view of an alternative septum assembly bore as may be included in the header of FIG. 6 and which includes an energy director extending from an outer surface of the header.

For example, FIG. 11 is a cross-sectional view of a portion of the header body 502 including the septum assembly bore 508 in which a triangular energy director 552 protrudes from the outer surface 503 of the header body 502 and extends circumferentially about the septum assembly bore 508.

Figure 12:
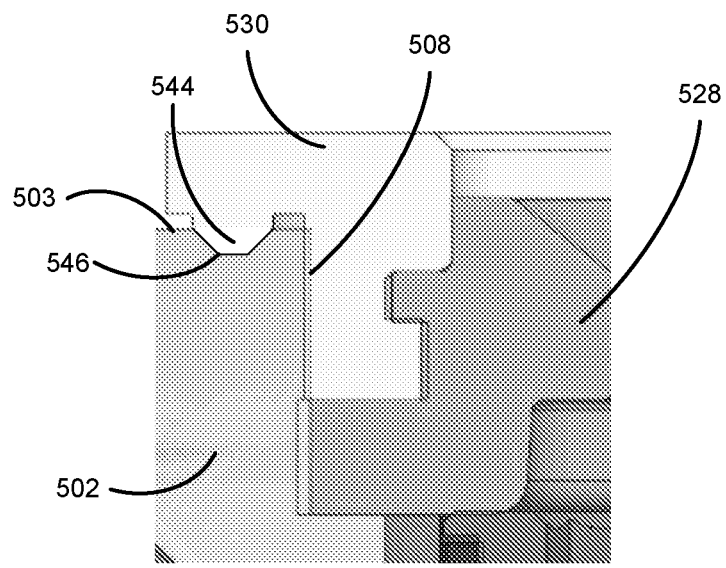
FIG. 12 is a detailed cross-sectional view of an alternative coupling arrangement between the retainer and header of FIG. 6 in which an energy director of the retainer is received within a groove of the header.

As another example, FIG. 12 illustrates a tongue-and-groove configuration in which the retainer 530 includes an energy director 544 in the form of a tongue that is received within a corresponding groove 546 defined in the outer surface 503 of the header body 502. In other configurations, the tongue may instead extend from the outer surface 503 of the header body 502 into a corresponding groove defined in the flange 540 of the retainer 530.

Figure 13:
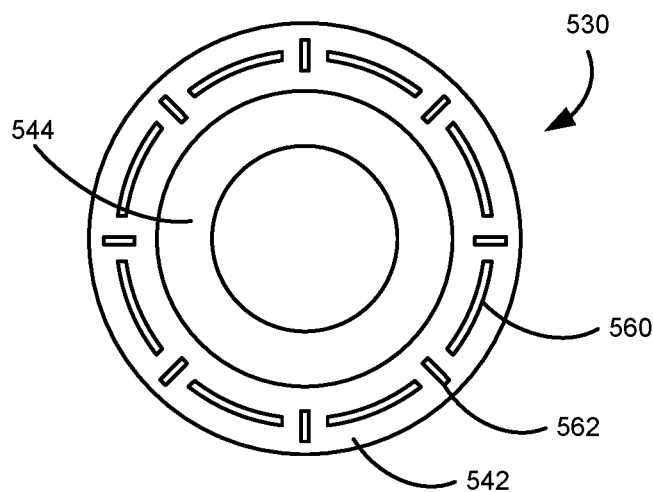
FIG. 13 is a bottom plan view of another alternative retainer for use in the septum assembly of FIG. 6, the alternative retainer including both radially and circumferentially extending energy directors.

Each of the configurations illustrated in FIGS. 9-12 generally include energy directors that extend continuously and circumferentially about either the flange 540 of the retainer 530 or the septum assembly bore 508. In other implementations, however, such energy directors may be discontinuous and/or extend, at least partially, in a radial direction. For example, FIG. 13 is a bottom view of the retainer 530 including both partial circumferential energy directors, such as energy director 560, and radial energy directors, such as energy director 562.

As previously noted, in certain implementations both the retainer 530 and the outer surface 503 of the header body 502 may include respective energy directors. Such energy directors may, in certain cases, cross or otherwise overlap. For example, radial energy directors of the flange 540 may cross circumferential energy directors of the outer surface 503 of the header body 502, or vice versa. In other implementations, one or more energy directors of the flange 540 may be positioned on the flange to extend between energy directors of the outer surface. In still other implementations, energy directors of the flange 540 may be disposed such that they do not intersect or interfere with energy directors of the outer surface 503. For example, the flange 540 may include a first energy director in the form of a ring having a first radius and the outer surface 503 may a second energy director in the form of a ring having a second radius different than the first radius.

In still other implementations, the retainer 530 and the outer surface 503 may include additional structural features to facilitate their joining. For example, one or both of the retainer 530 and the outer surface 503 may include a surface that is at least partially textured or roughened. In such implementations, the raised portions of the roughened surface function similarly to the more prominent energy directors discussed in previous examples.

Figure 14:
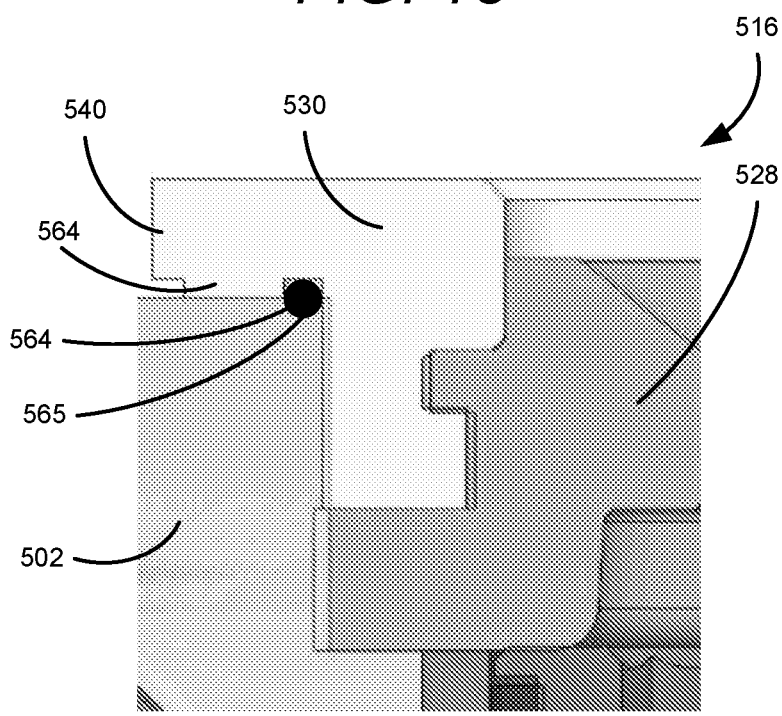
FIG. 14 is a detailed cross-sectional view of another alternative coupling arrangement between the retainer and header of FIG. 6 in which a sealing element is disposed between the retainer and the header body.

The process of welding the retainer 530 to the header body 502 may result in a continuous joint or bead that provides a seal about the circumference of the flange 540 or other interface between the retainer 530 and the header body 502. However, a sealing element may also be included between the retainer 520 and the header body 502 to provide a primary seal between the components or to provide a supplemental or backup seal to the joint between the retainer 530 and the header body 502. FIG. 14, for example, is a partial cross-sectional view of the septum assembly 516 as installed in the header body 502. As illustrated in FIG. 14, a sealing element 564 in the form of an O-ring 564 is disposed radially inward of the joint 566 formed between the retainer 530 of the septum assembly 516 and the header body 502. To facilitate retention of the sealing element 564 one both of the retainer 530 and the header body 502 may include a groove 565, cut-away, or similar structural feature within which the sealing element 564 may be retained. Although illustrated in FIG. 14 as being disposed between the flange 540 and the outer surface 503 of the header body 502, it should be appreciated that sealing elements may be at any suitable location between the retainer 530 and the header body 502 so as to prevent ingress of bodily fluid into the inner volume of the header assembly.

Figure 15:
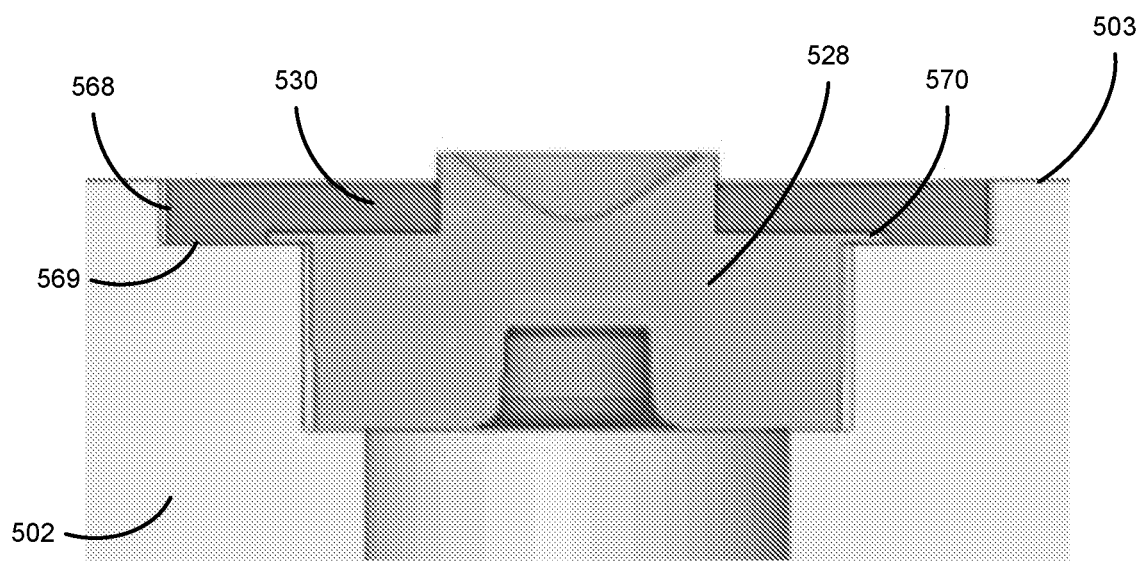
FIG. 15 is a detailed cross-sectional view of an alternative embodiment of the header assembly in which the retainer is received within a counter bore of the header body and the septum provides a sealing element.

FIG. 15 illustrates an alternative embodiment in which the header body includes a counter bore 568 shaped to receive the retainer 530. As a result, the retainer 530 may be at least partially disposed below the outer surface 503 of the header body 502. For example, in certain implementations, the retainer 530 may be received within the counter bore 568 such that the retainer 530 is substantially flush with the outer surface 503. In such implementations, the retainer 530 may be welded to a bottom 569 of the counter bore 568 as opposed to the outer surface 503 of the header body 502.

FIG. 15 further illustrates an alternative approach to forming a seal between the retainer 530 and the header body 502. In particular, the septum 528 of the septum assembly 516 includes a septum flange 570 that is disposed between the header body 502 and the retainer 530 when the retainer 530 is disposed within the counter bore 568. As pressure is applied to the retainer 530 during the ultrasonic welding process, the septum flange 570 is pinched between the retainer 530 and the header body 502, thereby forming a seal between the two components. It should be appreciated that the specific sealing configuration illustrated in FIG. 15 is merely one example and other arrangements in which a flange or other protrusion of the septum 528 is configured to extend between the retainer 530 and header body 502 are also contemplated.

Figure 16:
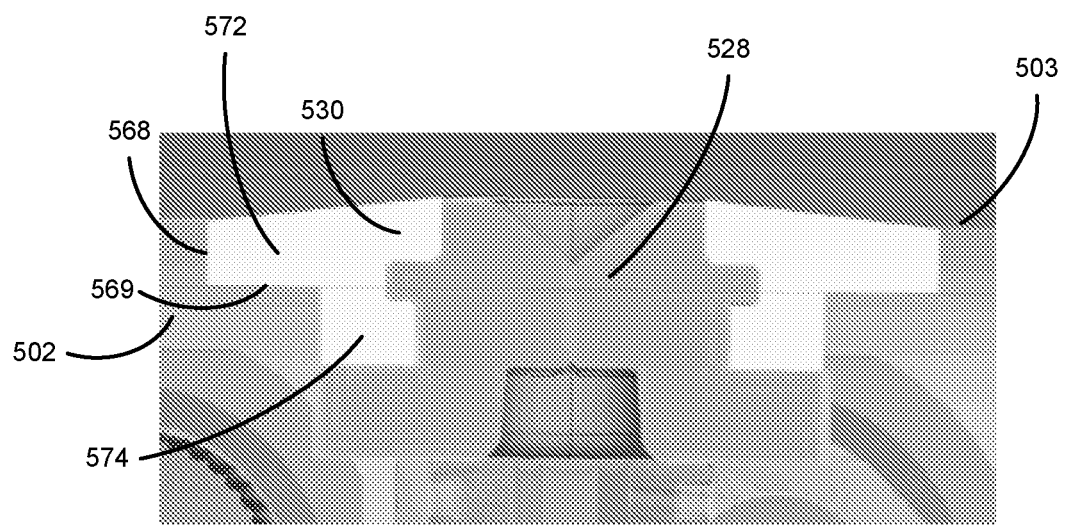
FIG. 16 is a detailed cross-sectional view of another alternative embodiment of the header assembly in which the retainer is received within a counter bore of the header body.

FIG. 16 is another example implementation of the header assembly 500 in which the retainer 530 of the septum assembly 516 is received such that a first portion 572 of the retainer is received within a counter bore 568 of the header body 502, while a second portion 574 extends further into the header body 502. In such implementations, the retainer 530 may be ultrasonically welded or otherwise joined to the bottom 569 of the counter bore 568. Similar to the implementation illustrated in FIG. 15, the retainer 530 is illustrated as being at least partially flush with the outer surface 503 of the header body 502.

Figure 17:
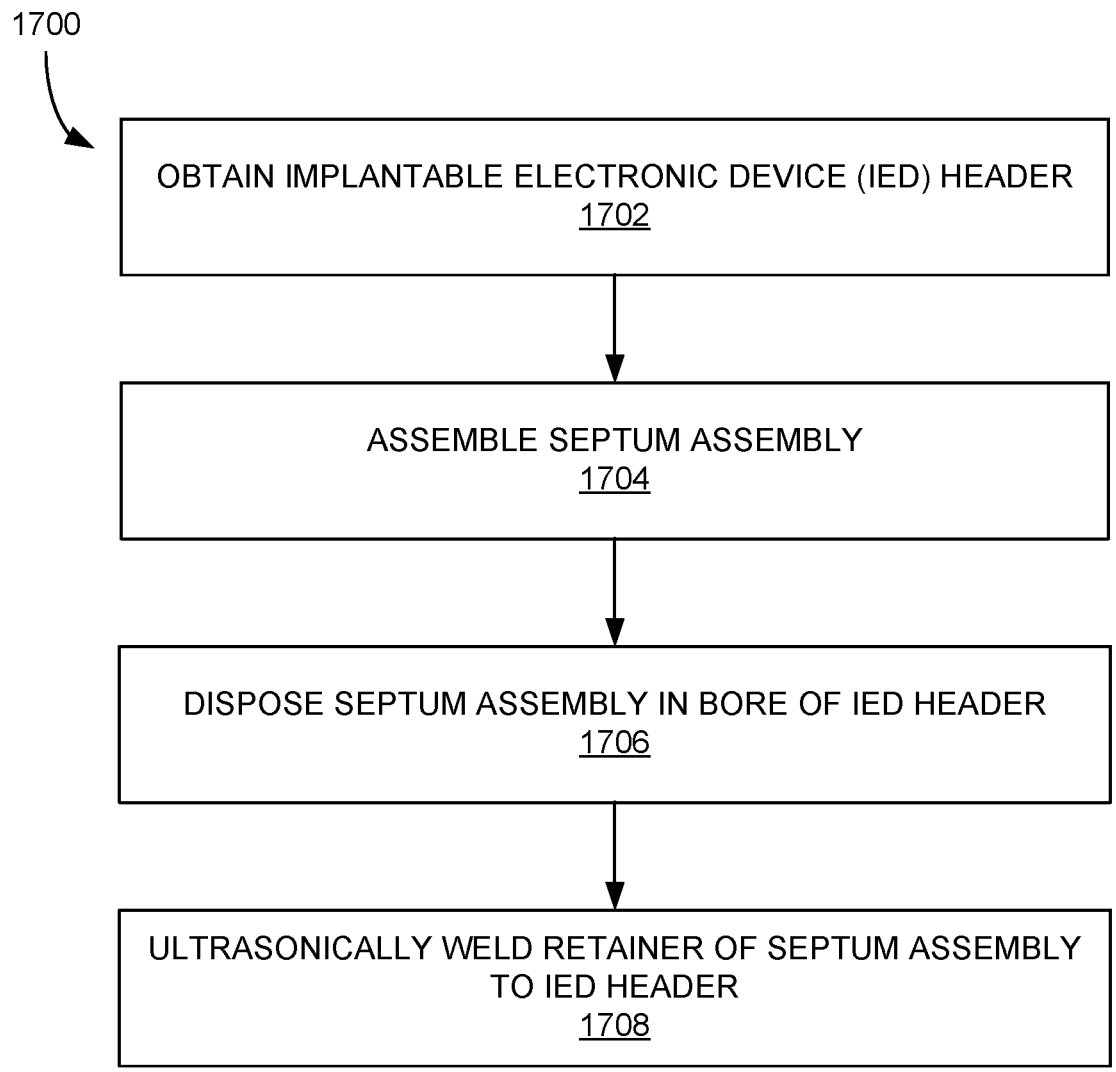
FIG. 17 is a flow chart illustrating a method of assembling a header of an implantable medical device including ultrasonically welded septum assemblies.

FIG. 17 is a flow chart illustrating an example method 1700 for assembling a header of an implantable electronic device (IED) and, more specifically, for installing one or more septums within a header of the IED.

At operation 1702, an IED header is obtained. Although the present disclosure is applicable to various configurations of IEDs and IED headers, in general, the IED header includes at least one bore extending from an outer surface of the IED header to an internal volume of the IED header. In at least some implementations, the bore may be used to access set screws for retaining terminal ends of leads within the IED header. When obtained, the IED header may be a standalone assembly or may already be coupled to an IED housing (e.g., a "can" including electronic components of the IED).

At operation 1704, a septum assembly is assembled. As previously discussed in the context of FIGS. 7-10, the septum assembly generally includes a flexible septum retained by a rigid retainer, each of which may include multiple parts. In certain implementations, the retainer may include channels, grooves, or similar structural features that mate with corresponding structural features of the septum.

At operation 1706, the septum assembly is disposed in a bore of the header. More specifically, the septum assembly is disposed within the bore of the header such that a surface of the retainer abuts a surface of the header and the septum is disposed within the header bore. In certain implementations, the retainer may include energy directors in the form of one or more protrusions, roughened surfaces, or similar structural elements. In such implementations, disposing the septum assembly within the bore of the header generally includes positioning the retainer such that the energy directors are made to contact a surface of the header.

In certain implementations, disposing the septum assembly in the bore of the header may further include placing a sealing element between the retainer and the header. As illustrated in FIG. 14, for example, an O-ring or similar sealing element may be disposed between the retainer of the septum assembly and the header. Alternatively, as illustrated in FIG. 15, a flange or similar portion of the septum may be configured to extend between the retainer and the header such that the septum provides a seal.

At operation 1708, the retainer of the septum assembly is ultrasonically welded to the header. To do so, a sonotrode (or similar tool for delivering ultrasonic energy to the septum assembly) is pressed into contact with the retainer of the septum assembly. With pressure maintained on the sonotrode, ultrasonic energy is provided to the sonotrode and transferred to the retainer. Such energy causes at least a portion of the retainer (e.g., an energy director of the retainer) and an abutting portion of the header to melt and comingle such that when the ultrasonic energy is no longer provided to the sonotrode, the comingled material cools to join the retainer and the header.

Following ultrasonic welding of the retainer to the header, installation of the septum assembly is substantially complete. The foregoing process for installing a septum assembly may then be repeated for any number of additional bores of the IED header that may require a septum assembly. When properly installed, the septum of the septum assembly, the weld joint formed between the retainer and the header, and any sealing elements disposed between the retainer, alone or in combination, effectively seal the IED bore such that fluid is prevented from entering the IED header through the bore. However, the septum generally permits insertion of elongate tools through the septum. For example, in one implementation, the septum may be adapted to permit insertion of a torque driver that may be used to tighten or loosen set screws disposed within the IED header.

C. Header Assemblies Including Laser-Welded Septum Assemblies

As noted above, coupling of a septum assembly to a header of the IED may be conducted in various ways. For example, in the previously discussed implementations of this disclosure, ultrasonic welding was implemented as the primary method for coupling a retainer of the septum assembly to the header of the IED. In another implementation discussed in further detail below, laser welding may instead be used to join a septum assembly to an IED header.

In one example implementation, the retainer of the septum assembly is disposed within the IED header such that a surface of the retainer abuts a surface of the IED header. The retainer is generally formed from a laser-permeable thermoplastic material such that a laser may be passed through the retainer to weld the surface of the retainer to the surface of the IED header. In certain implementations, such welding is achieved without the need for adhesives, additives, or coatings applied to either the retainer or header. However, in other implementations, additives or coatings may nevertheless be applied to the retainer or header to facilitate laser welding.

Although the particular laser used to weld the septum assembly to the IED header may vary, in at least one example implementation a two-micron fiber laser (such as a thulium nanosecond pulsed fiber laser) may be used. Such wavelengths generally correspond to lasers that exhibit good penetration into the thermoplastic material of the retainer to allow sub-surface clear-to-clear weld joining of the retainer to the IED header.

The foregoing and other aspects of the present disclosure are provided below in further detail. However, it should be appreciated that unless otherwise specified, general aspects of IEDs, IED headers, and septum assemblies previously discussed in this disclosure generally apply to implementations in which septum assemblies are laser-welded to IED headers.

Figure 18:
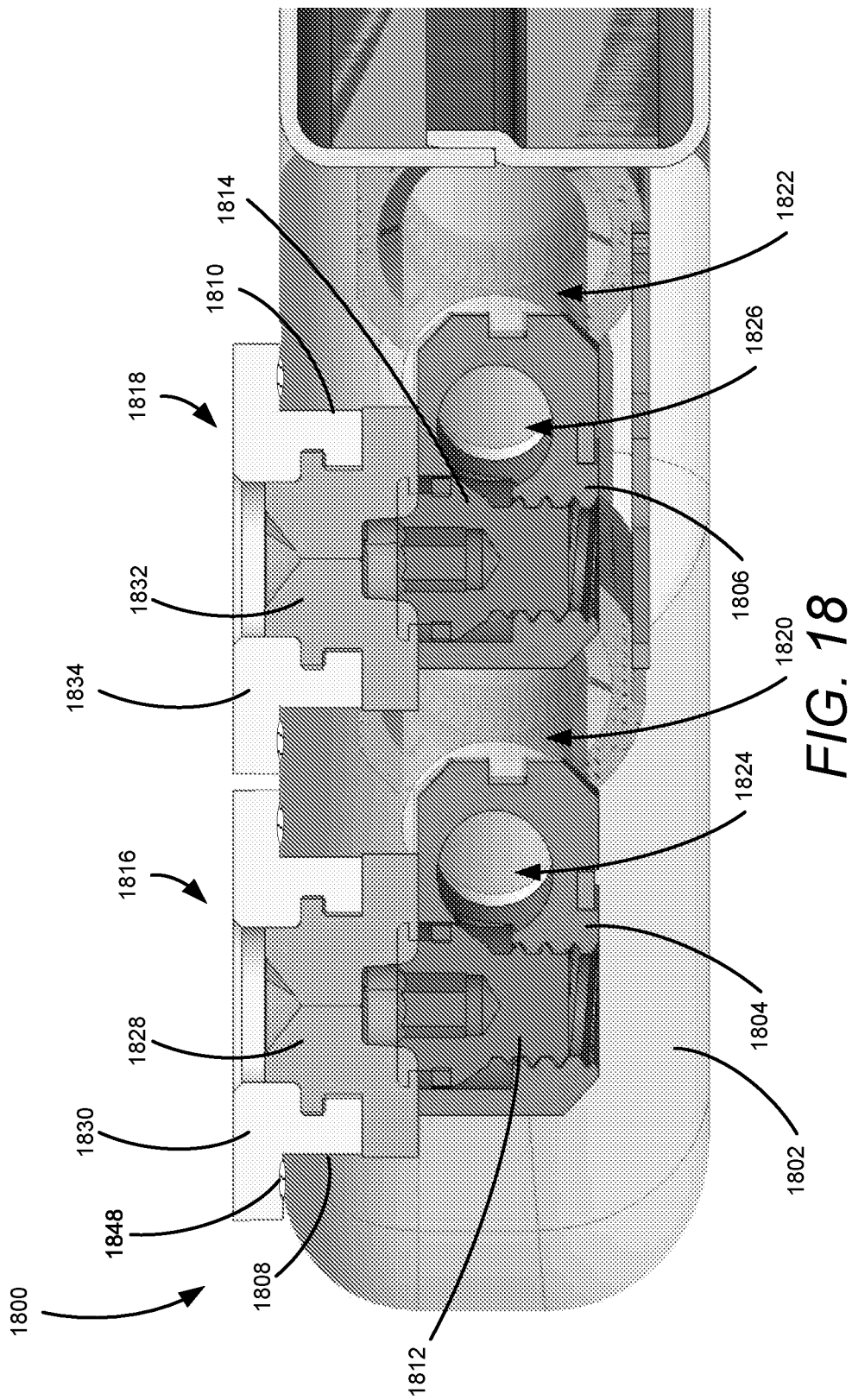
FIG. 18 is a cross-sectional view of an header including laser-welded septum assemblies.

FIG. 18 is a partial cross-sectional view of a header assembly 1800 in accordance with the present disclosure. As illustrated, the header assembly 1800 includes a header body 1802 within which a pair of tip blocks 1804, 1806 is disposed. The tip blocks 1804, 1806 are configured to receive a lead tip, such as the tip terminal 12 of the connector end 11 illustrated in FIG. 1. The header body 1802 defines septum bores 1808, 1810 within which set screws 1812, 1814 and septum assemblies 1816, 1818 may be disposed. The septum bores 1808, 1810 may extend perpendicular to connector bores 1820, 1822 such that the set screws 1814, 1816 are disposed adjacent to connector tip receiving bores 1824, 1826 of the tip blocks 1804, 1806.

The septum assemblies 1816, 1818 are configured to enable insertion of a tool for rotating and counter-rotating the set screws 1812, 1814 and to provide a seal when the tool is not present. More specifically, in the illustrated example, a first septum assembly 1816 includes each of a first flexible septum 1828 and a first retainer 1830 while a second septum assembly 1818 includes each of a second flexible septum 1832 and a second retainer 1834. Reference in the following discussion is made to the first septum assembly 1816; however, it should be understood that details of the first septum assembly generally apply to the second septum assembly 1818 unless otherwise noted. The header assembly 1800 may include more or fewer set screws than illustrated in FIG. 18 and, as a result, more or fewer septum assemblies.

Figure 19:
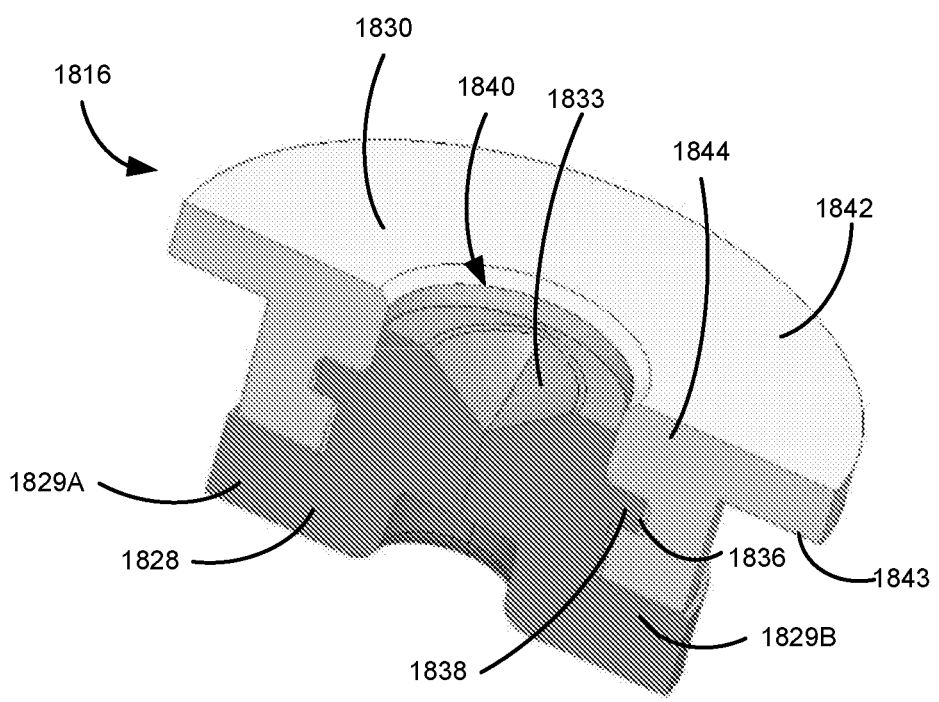
FIG. 19 is an isometric cross-sectional view of a retainer of the septum assembly of FIG. 18.
Figure 20:
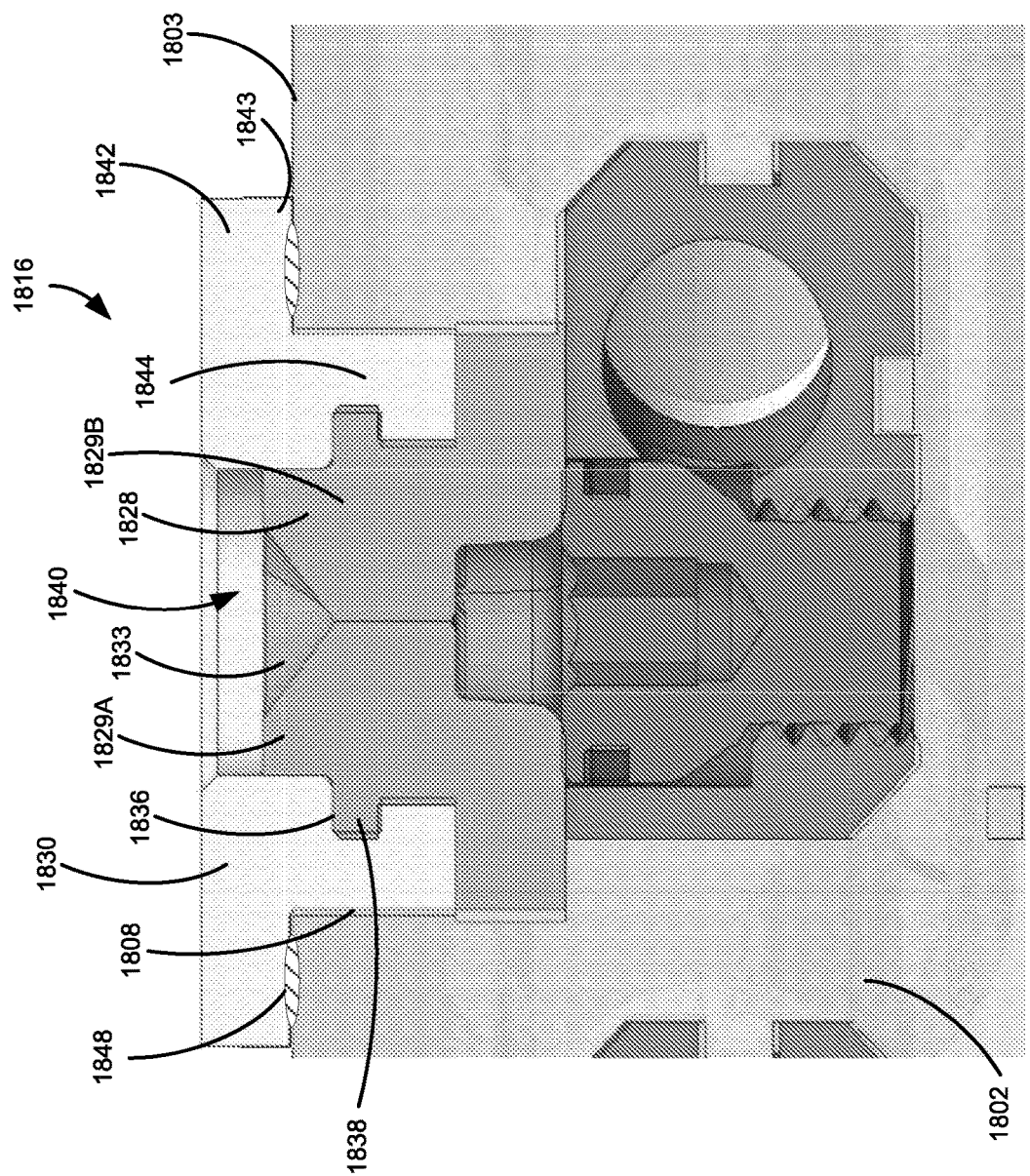
FIG. 20 is a detailed cross-sectional view of the septum assembly of FIG. 18.

Reference is now made to FIGS. 19 and 20, which provide additional details regarding the septum assembly 1816. FIG. 19 is an isometric cross-sectional view of the septum assembly 1816 while FIG. 20 is a detailed view of the septum assembly 1816 as disposed within the header body 1802 of the header assembly shown in FIG. 18.

Similar to previously discussed implementations, the septum assembly 1816 includes each of a septum 1828 and a retainer 1830. The septum 1828 is generally formed of a flexible material and may be split into two or more pieces (e.g., a first septum half 1829A and a second septum half 1829B). The septum 1828 further includes a puncture or slit extending through the septum 1828 to enable insertion of tools through the septum 1828 and may include a guide surface 1833 for directing tools toward the center of the septum 1828.

The retainer 1830 of the septum assembly 1816 retains the septum 1828 and couples the septum assembly to the header body 1802. With respect to retaining the septum 1828, the retainer 1830 may include channels, grooves, or similar features that mate with corresponding features of the septum 1828. For example, the retainer 1830 may include an inner circumferential groove 1836 within which an outer circumferential protrusion 1838 of the assembled septum 1828 is inserted. The retainer 1830 further defines a bore 1840 extending therethrough such that a tool may access the septum 1828.

In implementations of the present disclosure, the retainer 1830 is coupled to the header body 1802 by laser welding a feature or surface of the retainer 1830 that abuts a corresponding surface or feature of the header body 1802 when the septum assembly 1816 is inserted into the septum assembly bore 1808. To facilitate such welding, each of the retainer 1830 and the header body 1802 may be formed from the same transparent or translucent thermoplastic material. Alternatively, each of the retainer 1830 and the header body 1802 may be formed of different but weldable materials. In one specific implementation, either or both of the retainer 1830 and the header body 1802 may be formed from thermoplastic polyether polyurethane, such as Elasthane™. Other example thermoplastic polyether polyurethanes include, without limitation Pellethane™ and Tecothane™. In other applications, the header body 1802 and retainer 1830 may be formed of other materials, such as a polycarbonate urethane (e.g., Bionate™).

In the specific example illustrated in FIGS. 19 and FIG. 20, the retainer 1830 includes a flange 1842 that extends radially outward from a body 1844 of the retainer 1830. When the septum assembly 1816 is disposed within the septum assembly bore 1808, the flange 1842 extends beyond the septum assembly bore 1808 and abuts an outer surface 1803 of the header body 1802. When so positioned, a welding surface 1843 of the flange 1842 may be joined to the outer surface 1803 of the header body 1802 by laser welding, fixing the septum assembly 1816 to the header body 1802. For example, as illustrated in each of FIGS. 18 and 20, laser welding of the retainer 1830 to the header body 1802 generally results in a weld 1848 formed at an interface between the retainer 1830 and the header body 1802. In addition to joining the retainer 1830 and the header body 1802, the weld 1848 may also form a seal, preventing ingress of bodily fluid into the header.

Figure 22:
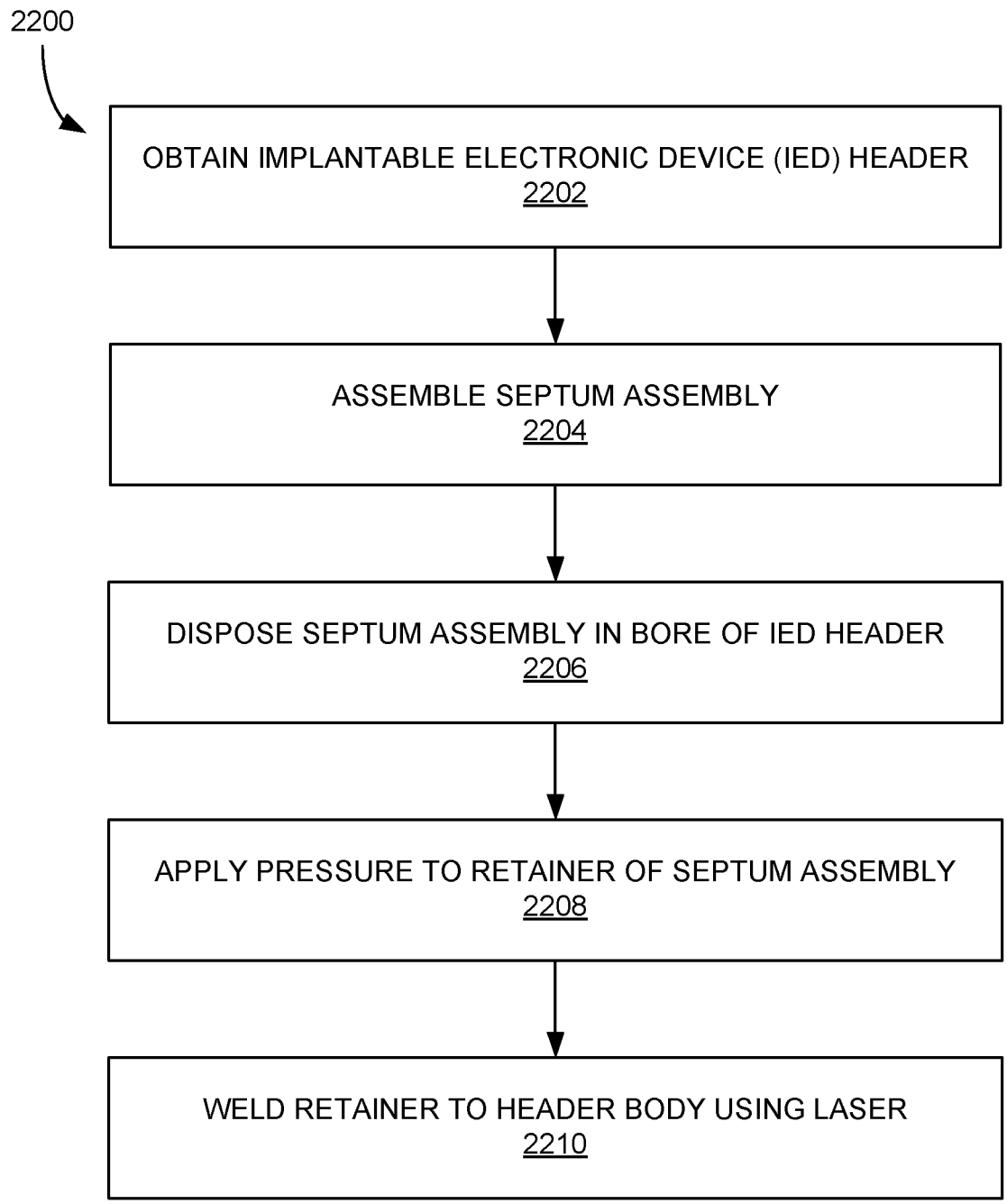
FIG. 22 is a flow chart illustrating a method of assembling a header of an implantable medical device including ultrasonically welded septum assemblies.

An example process for laser welding the septum assembly 1816 to the header body 1802 is illustrated in FIGS. 21A-21D. The process illustrated in FIGS. 21A-21D is also summarized in the FIG. 22, which is a flow chart of a method 2200 of manufacturing an IED.

At operations 2202 and 2204, an IED header is obtained and the septum assembly 1816 is assembled (e.g., by inserting the septum 1828 into the retainer 1830). At operation 2206 and as illustrated in FIG. 21A, the septum assembly 1816 is then disposed in the bore 1808 defined in the header body 1802. More specifically, the septum assembly 1816 is disposed within the bore 1808 such that the retainer 1830 abuts the header body 1802 and the septum 1828 is disposed within the bore 1808.

At operation 2208 and as illustrated in FIG. 21B, pressure may be applied to the retainer 1830 to improve contact between the retainer 1830 and the header body 1802. In the example implementation illustrated in FIG. 21B, such pressure is applied by a plate 2102. The plate 2102 may be formed of glass or another similar material that is substantially transparent to the welding laser such that the welding laser may pass through the plate 2102 with minimal distortion, diffusion, attenuation, or other similar changes.

At operation 2210 and as illustrated in FIG. 21C, the retainer 1830 is laser-welded to the header body 1802 by a welding laser 2104. In general, the process of laser welding the retainer 1830 includes directing the welding laser 2104 through the retainer to an interface between the retainer 1830 and the header body 1802. The welding laser 2104 is directed along a path that extends about the retainer 1830 such that the welding laser 2104 heats material of each of the retainer 1830 and the header body 1802, forming a weld/bead 1848 (shown in FIG. 21D) forms and joining the retainer 1830 to the header body 1802.

In one specific test of an implementation of the present disclosure, each of the header body 1802 and the retainer 1830 were formed from Elasthane™ and the welding laser 2104 was a two-micron thulium nanosecond pulsed fiber laser. Although other laser settings are possible, welding was conducted with a laser power of 75 W, a beam size of approximately 3.6 mm, and a focused spot diameter of 150 um. The welding laser 2104 was moved about the retainer 1830 at a linear scan speed of approximately 150 mm/s and five passes were made about the circumference of the retainer 1830. Based on the size of the retainer 1830, the welding process lasted approximately 15 seconds and resulted in the weld 1848 being approximately 1 mm in width. During subsequent testing, it was observed that such welding resulted in bonding between the retainer 1830 and the header body 1802 that was approximately four times greater than conventional adhesive/epoxy-based techniques.

As illustrated in FIG. 21D, when the weld 1848 is completed, the welding laser 2104 may be deactivated and the plate 2102 may be removed. The foregoing process of inserting a septum assembly into a bore of the header body and laser welding the retainer of the septum assembly to the header body may then be repeated for any other septum assemblies to be installed.

IED headers including laser-welded septum assemblies in accordance with the present disclosure may also incorporate features previously discussed in the context of the ultrasonically welded septum assemblies. For example, similar to the implementation discussed in the context of FIG. 6, the header may include an insert to which the septum assembly is welded. In another example similar to implementations discussed in the context of FIGS. 15 and 16, the retainer of laser-welded septum assemblies may be disposed at least partially within a counter bore defined in the header body and welded to a bottom surface of the counter bore. As yet another example and similar to the implementations discussed in the context of FIGS. 14 and 15, a seal element (e.g., an O-ring or a flange of the septum) may be disposed between the retainer and the header body to provide further protection from ingress of fluid into the header. More generally, it should be appreciated that, with the exception of the septum assembly being laser welded versus ultrasonically welded, aspects of the implementations discussed above in the context of FIGS. 5-17 are generally applicable to implementations of the present disclosure including laser-welded septum assemblies. Accordingly and unless otherwise noted, any details or particular arrangements discussed in the context of ultrasonically welded implementations should be considered to equally apply to laser-welded implementations of the present disclosure.

Figure 23:
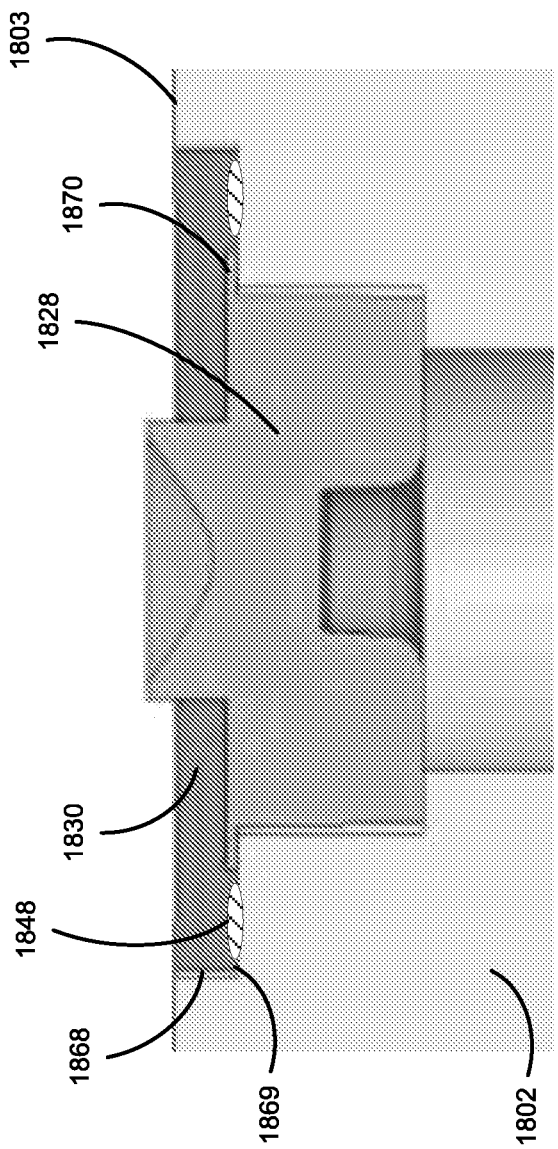
FIG. 23 is a detailed cross-sectional view of an alternative embodiment of a header assembly in which a retainer is received within a counter bore of the header body and the septum provides a sealing element.

In one specific example, FIG. 23 illustrates an alternative embodiment in which the header body 1802 includes a counter bore 1868 shaped to receive the retainer 1830. As a result, the retainer 1830 may be at least partially disposed below the outer surface 1803 of the header body 1802. For example, in certain implementations, the retainer 1830 may be received within the counter bore 1868 such that the retainer 1830 is substantially flush with the outer surface 1803. In such implementations, the retainer 1830 may be welded to a bottom 1869 of the counter bore 1868 (as indicated by weld 1848) as opposed to the outer surface 1803 of the header body 1802.

The implementation of FIG. 23 further illustrates a seal between the retainer 1830 and the header body 1802 formed by a septum flange 1870 of the septum 1828. The septum flange 1870 is disposed between the header body 1802 and the retainer 1830 when the retainer 1830 is disposed within the counter bore 1868. As pressure is applied to the retainer 1830 during the welding process (e.g., during operation 2208 of FIG. 22), the septum flange 1870 is pinched between the retainer 1830 and the header body 1802, thereby forming a seal.

The foregoing merely illustrates the principles of the present disclosure. Various modifications and alterations to the described illustrative embodiments will be apparent to those skilled in the art in view of the teachings herein. It will thus be appreciated that those skilled in the art will be able to devise numerous systems, arrangements and methods which, although not explicitly shown or described herein, embody the principles of the disclosure and are thus within the spirit and scope of the present disclosure. From the above description and drawings, it will be understood by those of ordinary skill in the art that the particular embodiments shown and described are for purposes of illustrations only and are not intended to limit the scope of the present inventive subject matter. References to details of particular embodiments are not intended to limit the scope of the inventive subject matter.

What is claimed is:

1. An implantable medical device comprising:
   a header body defining a header bore that extends from an outer surface of the header body to an inner cavity of the header body;
   a septum assembly comprising:
      a retainer disposed at least partially within the header bore and defining a retainer bore, the retainer including a first welding surface that abuts a second welding surface of the header body at a joint, the first welding surface secured to the second welding surface via a weld bead along the joint to secure the retainer to the header body; and
      a septum disposed at least partially within the retainer bore, the septum formed of a flexible material and defining at least one of a puncture or a slit therethrough to allow insertion of a tool through the septum into the inner cavity and to provide a seal when the tool is not inserted through the septum; and
   a sealing element disposed between the retainer and the header body along the joint to seal the joint, the sealing element discrete from the septum.

2. The implantable medical device of claim 1, wherein the sealing element is an O-ring.

3. The implantable medical device of claim 1, wherein at least one of the retainer or the header body defines a groove along the respective first welding surface or the second welding surface, and the sealing element is disposed within the groove.

4. The implantable medical device of claim 1, wherein the sealing element is disposed radially inward of the weld bead.

5. The implantable medical device of claim 1, wherein the retainer includes a retainer body and a flange extending from the retainer body, the retainer body defining the retainer bore, the flange including the first welding surface.

6. The implantable medical device of claim 1, wherein the second welding surface of the header body is a portion of the outer surface.

7. The implantable medical device of claim 1, wherein the header bore of the header body includes a counter bore, and the second welding surface is a bottom surface of the counter bore.

8. The implantable medical device of claim 1, wherein an entirety of the septum is recessed below the outer surface of the header body.

9. The implantable medical device of claim 1, further comprising a set screw disposed within the inner cavity.

10. The implantable medical device of claim 1, wherein the header body and the retainer are both composed of thermoplastic polyether polyurethane.

11. The implantable medical device of claim 1, wherein the retainer defines an inner circumferential groove along the inner circumferential surface, the septum including an outer circumferential protrusion that extends into the inner circumferential groove of the retainer.

12. An implantable medical device comprising:
a header body defining a header bore that extends from an outer surface of the header body to an inner cavity of the header body, the header bore including a counter bore;
a septum assembly comprising:
a retainer disposed at least partially within the counter bore and abutting a bottom surface of the counter bore, the retainer defining a retainer bore, the retainer including a first welding surface that abuts a second welding surface of the header body at a joint, the first welding surface secured to the second welding surface via a weld bead along the joint to secure the retainer to the header body; and
a septum formed of a flexible material and disposed at least partially within the retainer bore, the septum including a septum body and a septum flange extending from the septum body, the septum body defining at least one of a puncture or a slit therethrough to allow insertion of a tool through the septum into the inner cavity and to provide a seal when the tool is not inserted through the septum, the septum flange pinched between the retainer and the bottom surface of the counter bore along the joint to seal the joint.

13. The implantable medical device of claim 12, wherein the septum flange extends radially outward from an outer perimeter of the septum body.

14. The implantable medical device of claim 13, wherein a first portion of the septum body is disposed above the septum flange and a second portion of the septum body is disposed below the septum flange.

15. The implantable medical device of claim 12, wherein the retainer defines an inner circumferential groove along an inner circumferential surface of the retainer, the septum including an outer circumferential protrusion that extends into the inner circumferential groove of the retainer.

16. The implantable medical device of claim 12, wherein an entirety of the septum is recessed below the outer surface of the header body.

17. An implantable medical device comprising:
a header body defining a header bore that extends from an outer surface of the header body to an inner cavity of the header body;
a septum assembly comprising:
a retainer disposed at least partially within the header bore and including an inner circumferential surface that defines a retainer bore, the retainer including a first welding surface that abuts a second welding surface of the header body at a joint, the first welding surface secured to the second welding surface via a weld bead along the joint to secure the retainer to the header body, the retainer defining an inner circumferential groove along the inner circumferential surface; and
a septum disposed at least partially within the retainer bore, the septum formed of a flexible material and defining at least one of a puncture or a slit therethrough to allow insertion of a tool through the septum into the inner cavity and to provide a seal when the tool is not inserted through the septum, the septum including an outer circumferential protrusion that extends into the inner circumferential groove of the retainer.

18. The implantable medical device of claim 17, further comprising a sealing element disposed between the retainer and the header body along the joint to seal the joint, the sealing element discrete from the septum.

19. The implantable medical device of claim 18, wherein the sealing element is an O-ring.

20. The implantable medical device of claim 17, wherein the septum includes a septum body and a septum flange extending from the septum body, the septum flange pinched between retainer and the header body along the joint to seal the joint.

* * * * *